US012564710B2

(12) United States Patent
Matthes et al.

(10) Patent No.: US 12,564,710 B2
(45) Date of Patent: Mar. 3, 2026

(54) SYSTEM FOR SECURING A RELEASABLE CONNECTION BETWEEN TWO ELEMENTS

(71) Applicant: Berlin Heart GmbH, Berlin (DE)

(72) Inventors: Michael Matthes, Atlandsberg (DE); Gerhard Lauterbach, Berlin (DE); Kim Peter Winterweber, Erlangen (DE); Maik Meissner, Nuthetal/Saarmund (DE)

(73) Assignee: Berlin Heart GmbH, Berlin (DE)

( * ) Notice: Subject to any disclaimer, the term of this patent is extended or adjusted under 35 U.S.C. 154(b) by 1418 days.

(21) Appl. No.: 16/346,981

(22) PCT Filed: Nov. 2, 2017

(86) PCT No.: PCT/EP2017/078104
§ 371 (c)(1),
(2) Date: May 2, 2019

(87) PCT Pub. No.: WO2018/083203
PCT Pub. Date: May 11, 2018

(65) Prior Publication Data
US 2020/0069855 A1 Mar. 5, 2020

(30) Foreign Application Priority Data

Nov. 4, 2016 (EP) ..................................... 16197294

(51) Int. Cl.
*A61M 60/859* (2021.01)
*A61M 60/178* (2021.01)
(Continued)

(52) U.S. Cl.
CPC ........ *A61M 60/859* (2021.01); *A61M 60/178* (2021.01); *A61M 60/216* (2021.01); *A61M 60/878* (2021.01)

(58) Field of Classification Search
CPC A61M 39/1011; A61M 60/50; A61M 60/268; A61M 60/859; A61M 60/878; A61M 60/178; A61M 60/216
See application file for complete search history.

(56) References Cited

U.S. PATENT DOCUMENTS 6,186,999 B1 2/2001 Chen
6,305,962 B1 * 10/2001 Maher .................... H01R 24/84
439/27

(Continued)

FOREIGN PATENT DOCUMENTS

CN 1235661 A 11/1999
CN 101360946 A 2/2009
(Continued)

OTHER PUBLICATIONS

Office Action and Search Report for Chinese Patent application No. 201780068275.0, dated May 8, 2021, China National Intellectual Property Administration, Beijing, People's Republic of China (with English translation) (18 pp.).

(Continued)

*Primary Examiner* — Rex R Holmes
*Assistant Examiner* — Jennifer L Ghand
(74) *Attorney, Agent, or Firm* — Crowell & Moring LLP

(57) ABSTRACT
A system, such as a blood pump system, is provided for securing a releasable connection between two elements, in particular between two cables or between two hollow bodies, said system comprising: a first connector and a second connector that is releasably connectable to the first connector, a securing sleeve which, when the first connector is connected to the second connector, is movable, by displacement of the securing sleeve relative to the first connector and relative to the second connector into a securing position in which the securing sleeve completely or at least partially receives the first connector and the second connector, and a (Continued)

latching device with at least one latching element, wherein the latching device is configured to produce a latching connection between the securing sleeve in the securing position and the first connector and/or the second connector connected to the first connector.

19 Claims, 23 Drawing Sheets

(51) Int. Cl.
A61M 60/216 (2021.01)
A61M 60/878 (2021.01)

(56) References Cited

U.S. PATENT DOCUMENTS

| | | | | |
|---|---|---|---|---|
| 6,893,055 B2 * | 5/2005 | Thomas | | F16L 37/084 |
| | | | | 285/369 |
| 8,652,024 B1 * | 2/2014 | Yanai | | A61M 39/1011 |
| | | | | 600/16 |
| 9,909,702 B2 * | 3/2018 | McCure | | F16L 21/08 |
| 10,737,007 B2 * | 8/2020 | Duhamel | | H01B 7/048 |
| 10,953,145 B2 * | 3/2021 | Petersen | | A61M 60/148 |
| 2009/0240326 A1 * | 9/2009 | Wilson | | A61F 2/2427 |
| | | | | 623/2.11 |
| 2012/0192968 A1 * | 8/2012 | Bonnal | | A61M 39/1011 |
| | | | | 137/454.2 |
| 2013/0096364 A1 * | 4/2013 | Reichenbach | | F04D 13/064 |
| | | | | 416/174 |
| 2014/0353966 A1 * | 12/2014 | Schmidt | | A61M 39/1011 |
| | | | | 285/330 |
| 2016/0363247 A1 * | 12/2016 | McCure | | F16L 37/12 |
| 2017/0000999 A1 * | 1/2017 | Dennis | | A61M 39/26 |
| 2017/0036007 A1 * | 2/2017 | Hallisey | | A61M 39/1011 |
| 2018/0311427 A1 * | 11/2018 | Duhamel | | A61M 60/871 |
| 2021/0199220 A1 * | 7/2021 | Truong | | F16L 37/32 |

FOREIGN PATENT DOCUMENTS

| | | | |
|---|---|---|---|
| CN | 100554749 C | 10/2009 |
| CN | 102132079 A | 7/2011 |
| CN | 102782245 A | 11/2012 |
| CN | 104981642 A | 10/2015 |
| CN | 205402037 U | 7/2016 |
| DE | 20214608 U1 | 12/2002 |
| DE | 103 21 309 A1 | 1/2004 |
| DE | 20 2011 004 090 U1 | 6/2011 |
| EP | 0890758 A2 | 1/1999 |
| EP | 1468192 B1 | 3/2006 |
| EP | 2287974 B1 | 10/2011 |
| EP | 2463569 A1 | 6/2012 |
| EP | 2500612 A1 | 9/2012 |
| EP | 3228336 A1 | 10/2017 |
| WO | WO 00/12164 | 3/2000 |
| WO | WO 2006/036192 A1 | 4/2006 |
| WO | WO 2012/126858 A1 | 9/2012 |
| WO | WO 2013/056131 A1 | 4/2013 |

OTHER PUBLICATIONS

International Search Report, issued in International Patent Application No. PCT/EP2017/078104, dated Jan. 15, 2018, pp. 1-3, European Patent Office, Rijswijk, Netherlands.

* cited by examiner

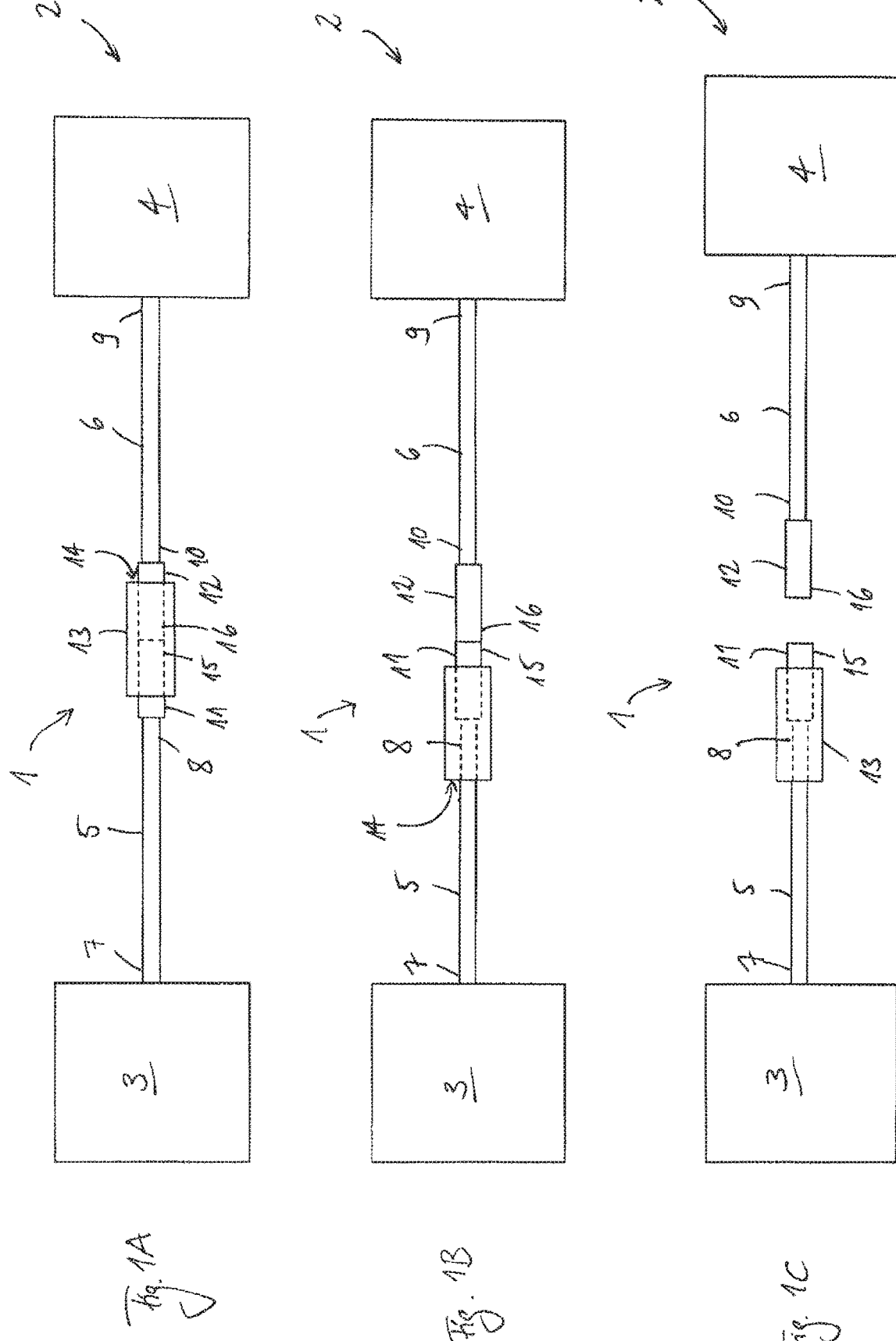

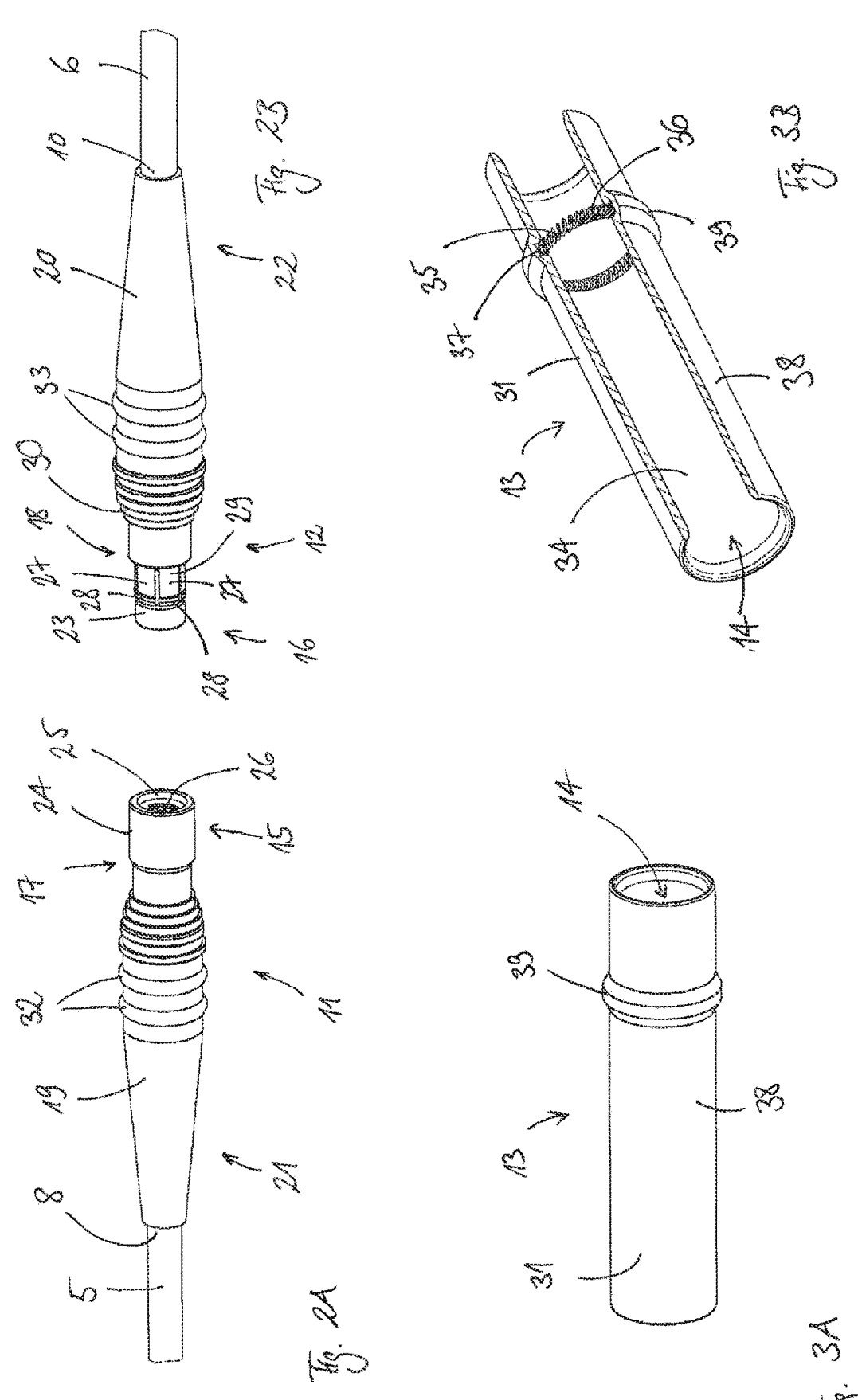

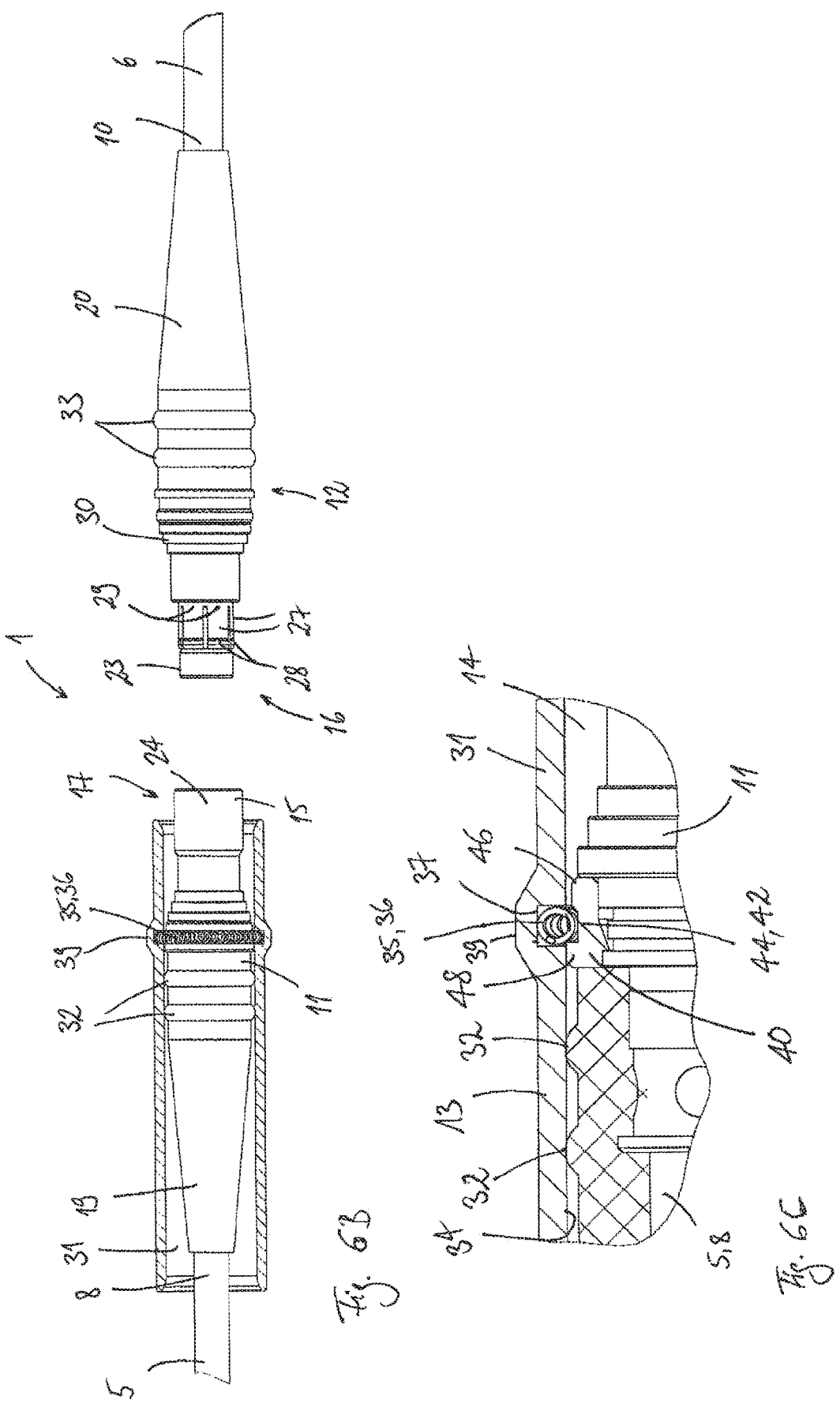

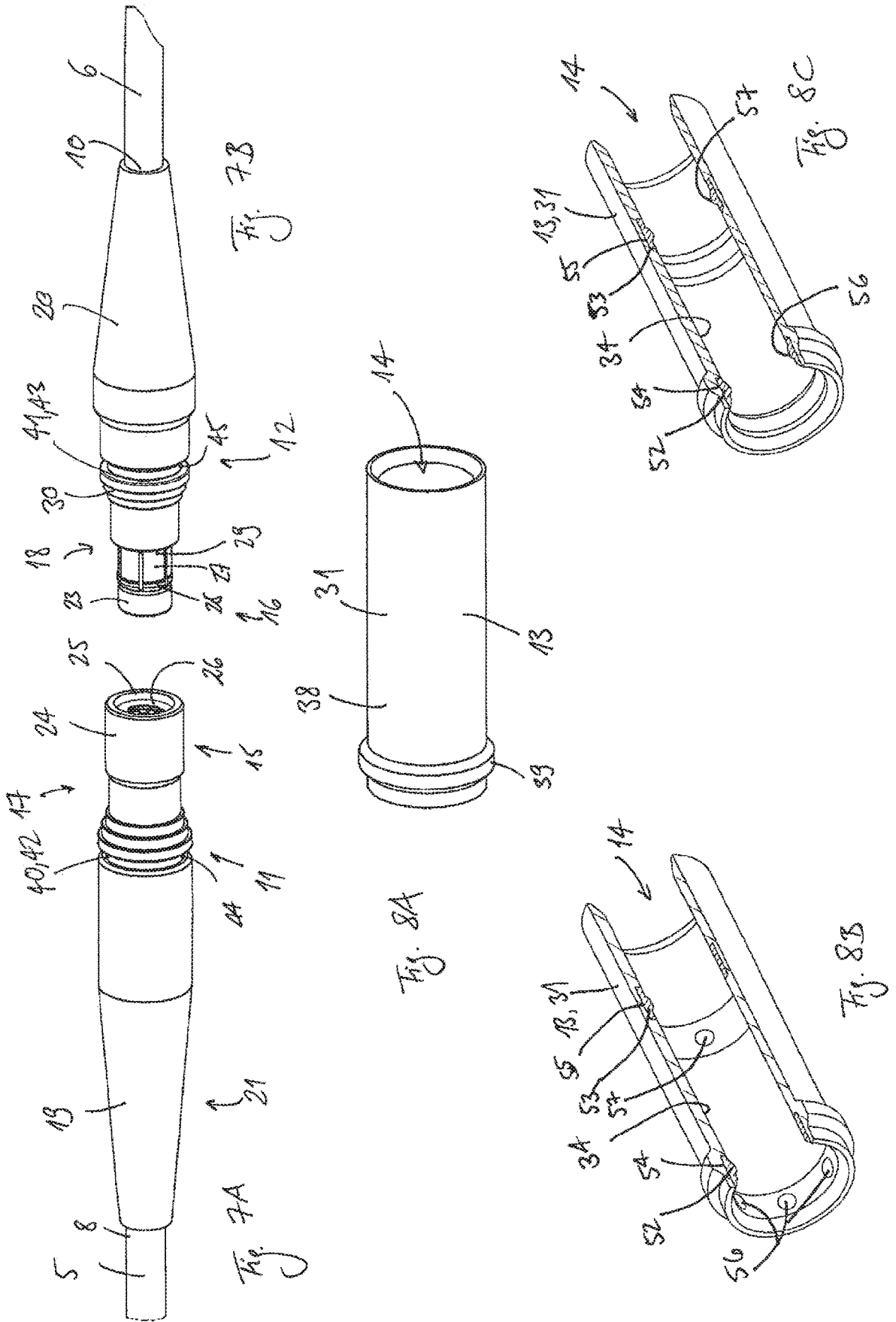

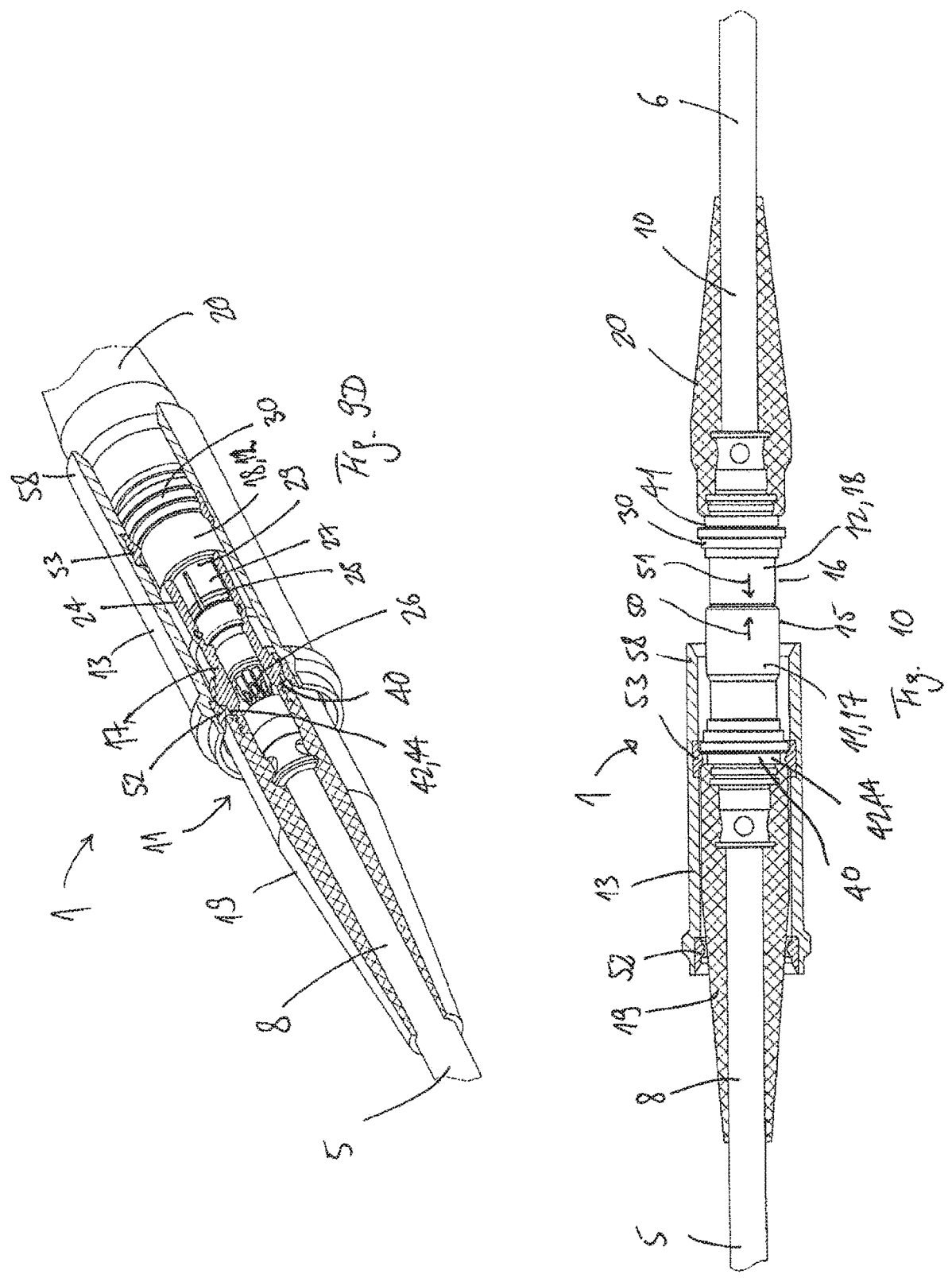

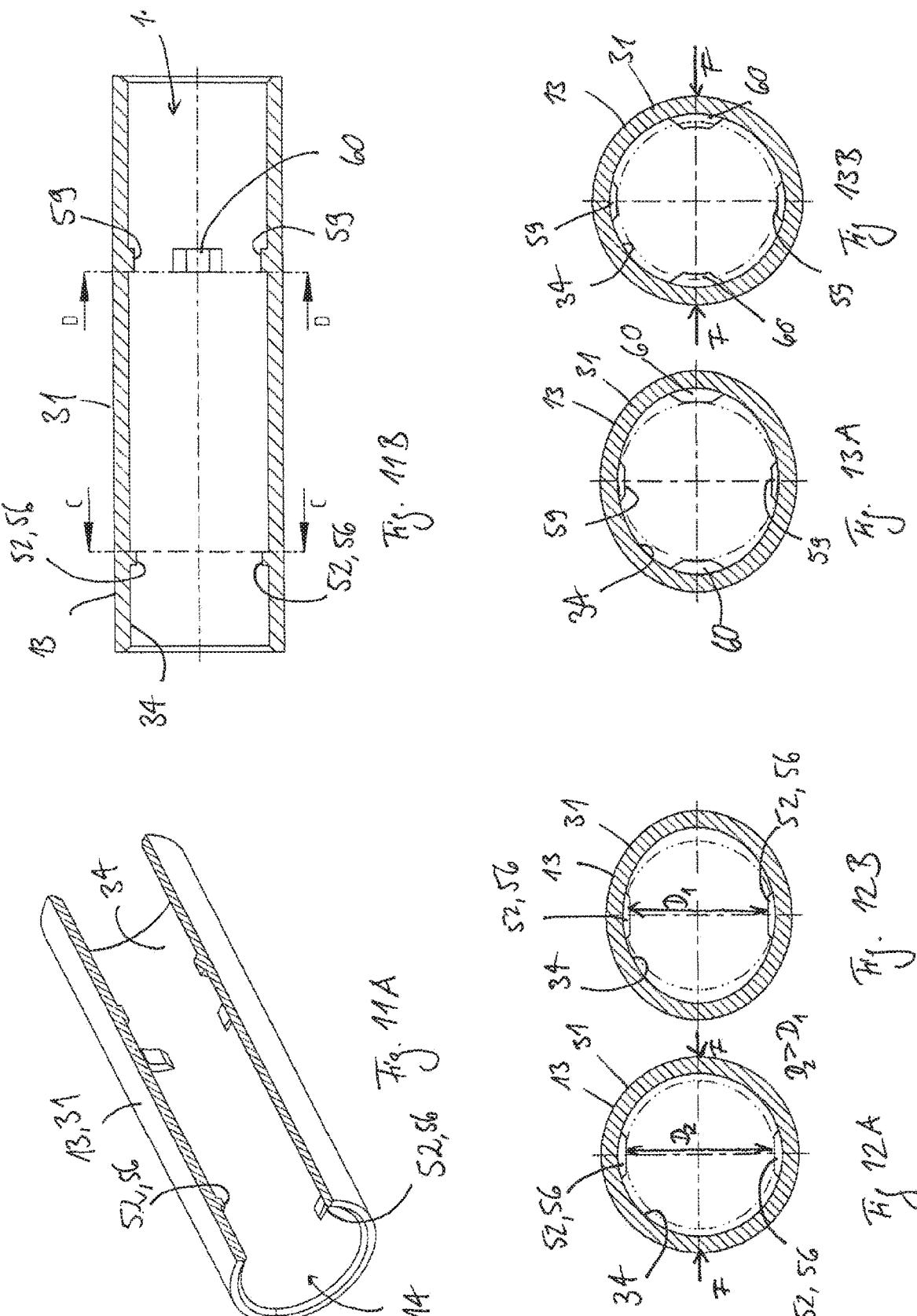

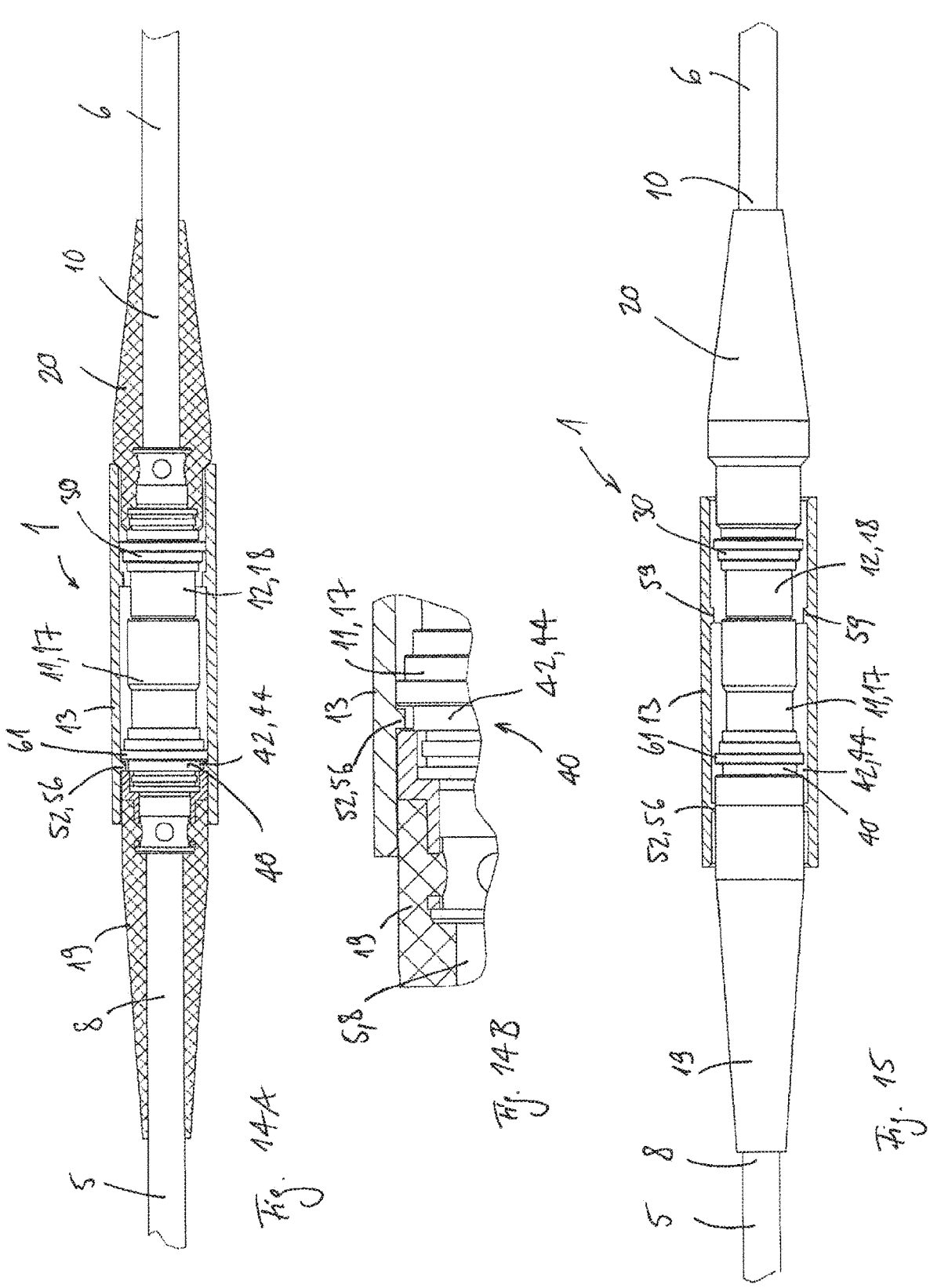

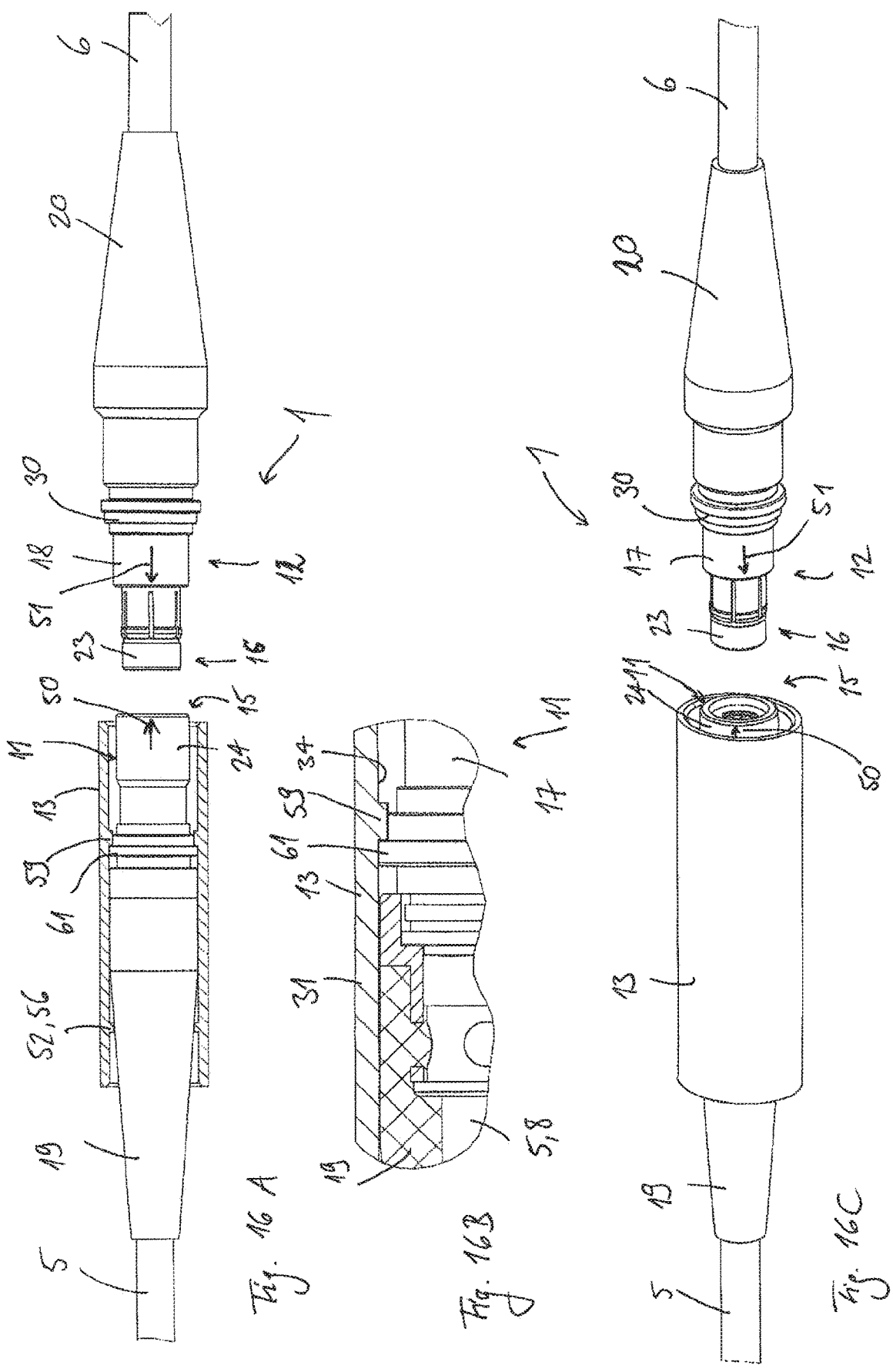

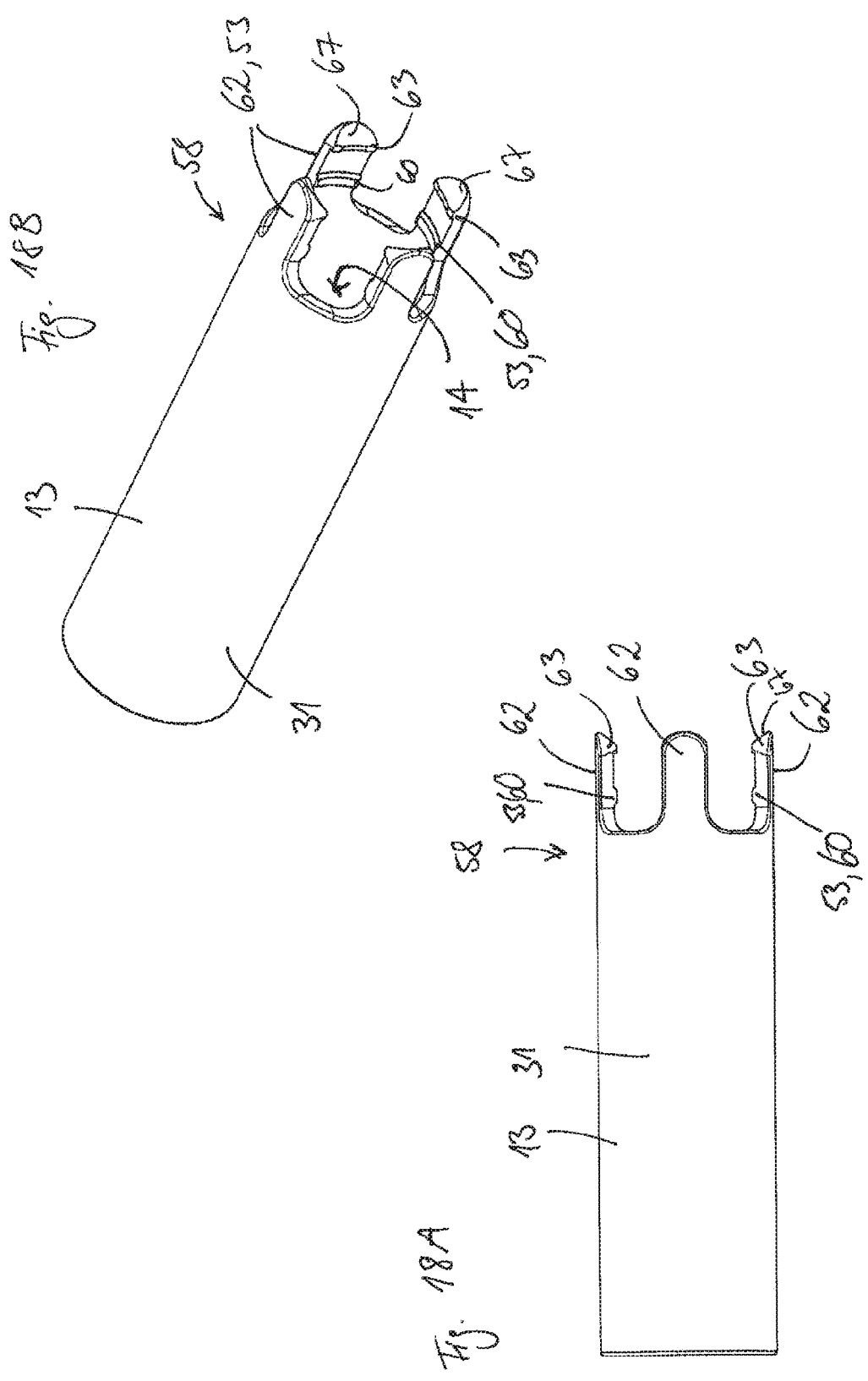

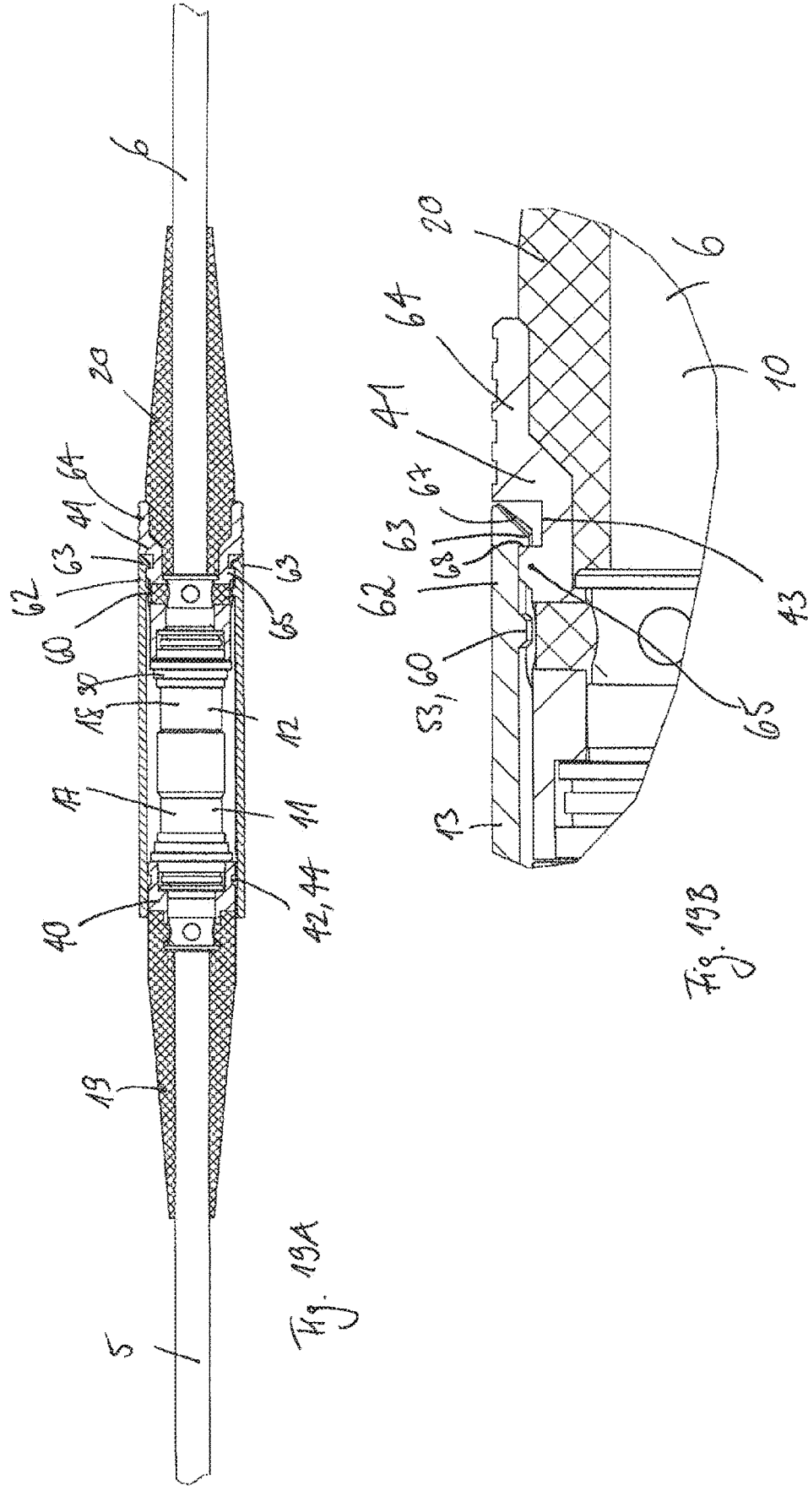

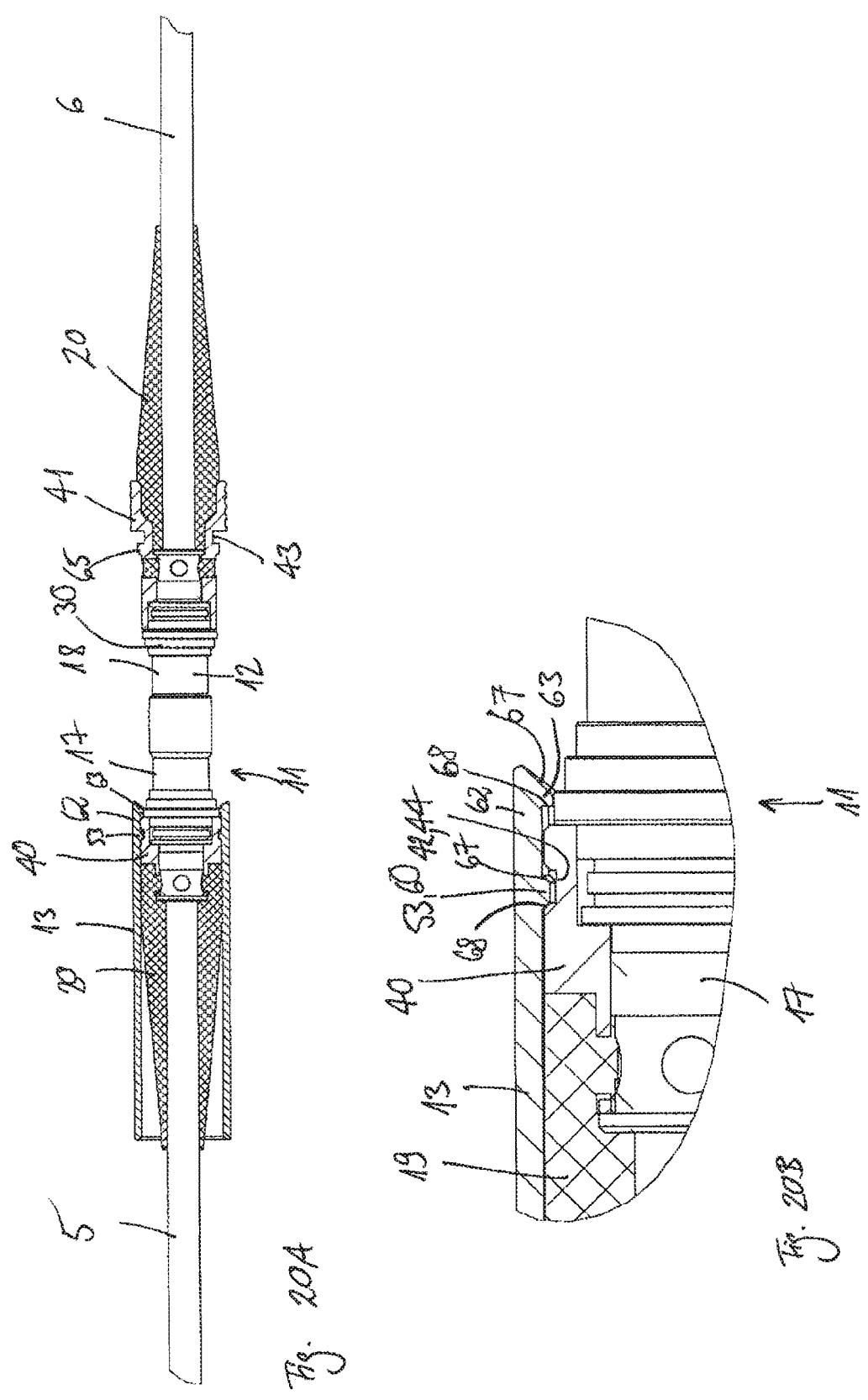

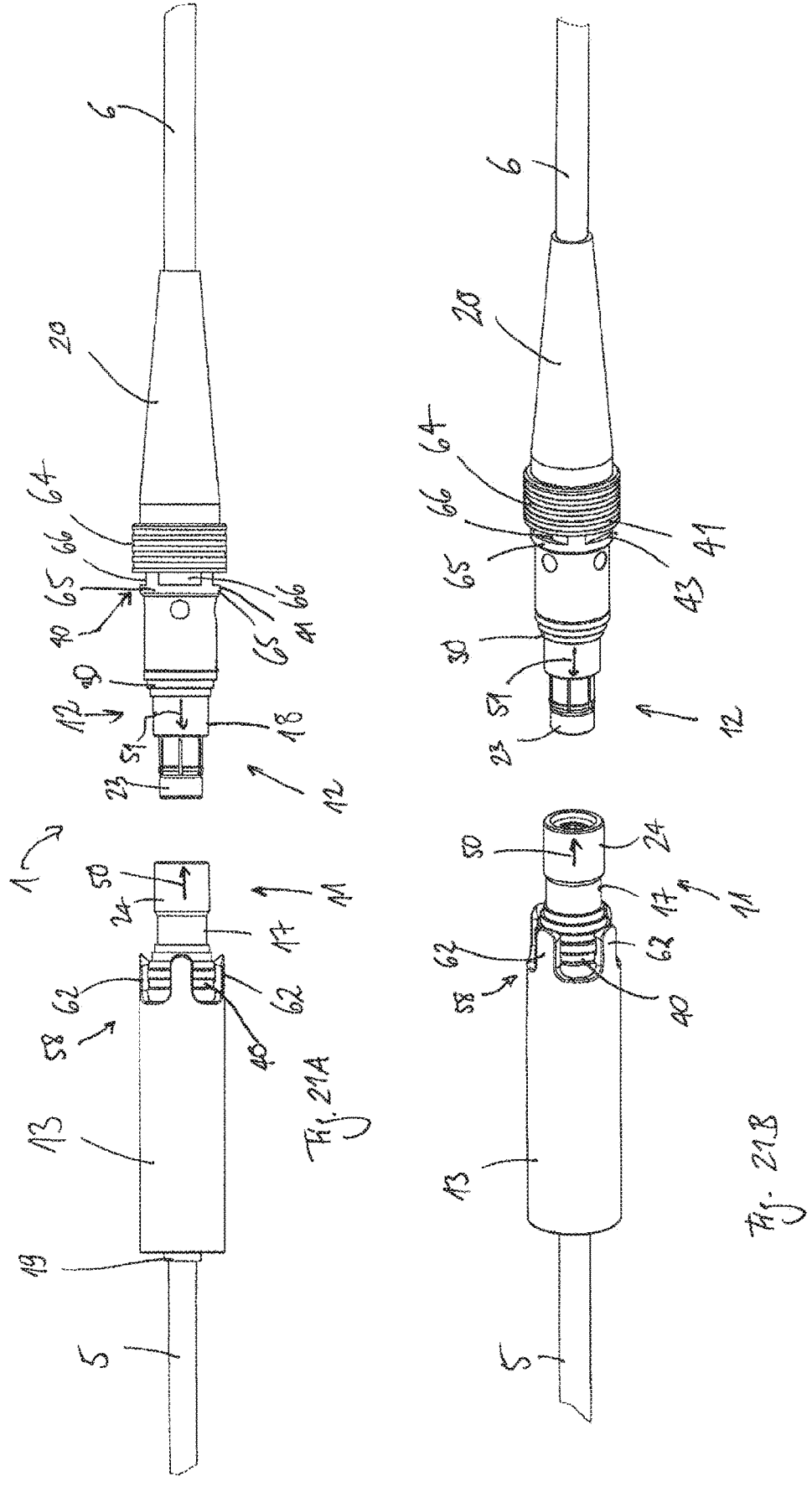

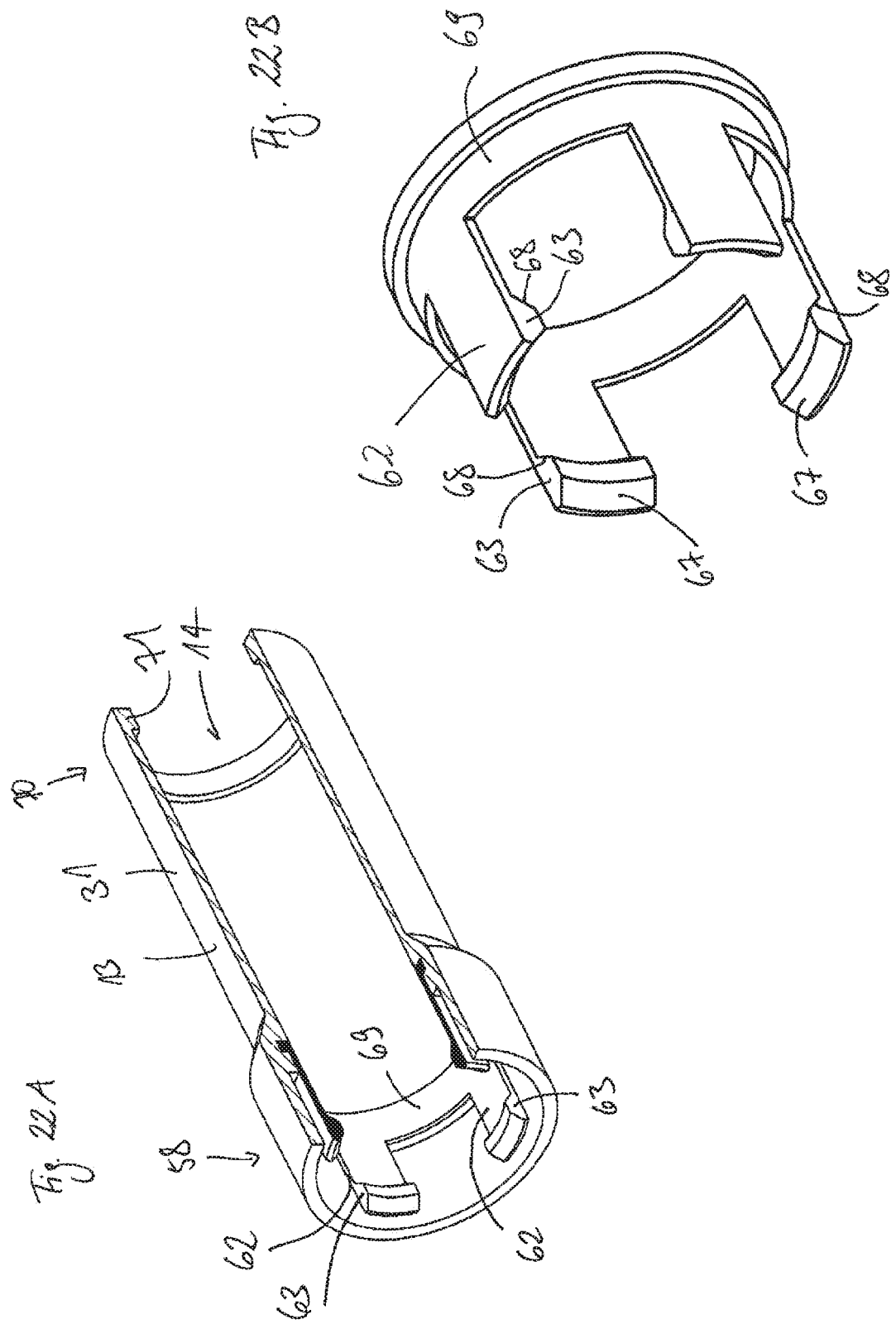

SYSTEM FOR SECURING A RELEASABLE CONNECTION BETWEEN TWO ELEMENTS

CROSS-REFERENCE TO RELATED APPLICATIONS

This application is a 371 nationalization of international patent application PCT/EP2017/078104 filed Nov. 2, 2017, which claims priority under 35 USC § 119 to European patent application 16197294.8 filed Nov. 4, 2016. The entire contents of each of the above-identified applications are hereby incorporated by reference.

BRIEF DESCRIPTION OF THE DRAWINGS

The figures are as follows:

FIG. 1A: a schematic illustration of a system of the type suggested here as a component of a blood pump system of the type suggested here in a connected and secured configuration;

FIG. 1B: the system and blood pump system shown in FIG. 1A in a connected and released configuration;

FIG. 1C: the system and blood pump system shown in FIGS. 1A and 1B in a separated configuration;

FIGS. 2A and 2B: perspective illustrations of a first sample embodiment (example 1) of the first connector and the second connector of the system shown in FIG. 1;

FIGS. 4A and 4B: sectional views of the connectors and the securing sleeve according to example 1 in a connected and secured configuration, wherein FIG. 4B illustrates an enlarged subarea of FIG. 4A;

FIG. 5 a sectional view of the connectors and the securing sleeve according to example 1 in a connected and released configuration;

FIG. 6A through 6C sectional views of, respectively, the connectors and one of the connectors and the securing sleeve according to example 1 in a separated configuration, wherein FIG. 6C illustrates an enlarged subarea of FIG. 6B;

FIGS. 7A and 7B: perspective illustrations of a second sample embodiment (example 2) of the first connector and the second connector, respectively, of the system shown in FIG. 1;

FIG. 8A through 8C: the securing sleeve of the system shown in FIG. 1 according to example 2, wherein FIG. 8A shows a perspective illustration of the sleeve and FIGS. 8B and 8C show sectional views of two possible variants of the sleeve;

FIG. 9A through 9D sectional views of the connectors and the securing sleeve according to example 2 in a connected and secured configuration, wherein FIGS. 9B and 9C each illustrate an enlarged subarea of FIG. 9A;

FIG. 10 a sectional view of the connectors and the securing sleeve according to example 2 in a connected and released configuration;

FIGS. 11A and 11B: the securing sleeve of the system shown in FIG. 1 according to a third sample embodiment (example 3), wherein FIG. 11A shows a perspective sectional view of the sleeve and FIG. 11B shows a lateral view of a longitudinal section through the sleeve;

FIGS. 12A and 12B: views of cross-sectional surfaces of the sleeve according to example 3 along the cutting plane marked in FIG. 11B and labeled as C-C, wherein 12A shows the sleeve in a tensioned intermediate state and 12B shows the sleeve in an untensioned initial state;

FIGS. 13A and 13B: views of cross-sectional surfaces of the sleeve according to example 3 along the cutting plane marked in FIG. 11B and labeled as D-D, wherein 13A shows the sleeve in an untensioned initial state and 13B shows the sleeve in a tensioned intermediate state;

FIGS. 14A and 14B: sectional views of the connectors and the securing sleeve according to example 3 in a connected and secured configuration, wherein FIG. 14B illustrates an enlarged subarea of FIG. 14A;

FIG. 15 sectional view of the connectors and the securing sleeve according to example 3 in a connected configuration, in which the sleeve is between the securing position and the holding position;

FIG. 16A through 16C sectional views or a perspective view of the connectors and the securing sleeve according to example 3 in a separated configuration, wherein FIG. 16B shows an enlarged sectional view of a subarea of the system;

FIGS. 18A and 18B: the securing sleeve of the system shown in FIG. 1 according to a fourth sample embodiment (example 4), wherein FIG. 18A shows a side view and FIG. 18B shows a perspective view of the sleeve;

FIGS. 19A and 19B: sectional views of the connectors and the securing sleeve according to example 4 in a connected and secured configuration, wherein FIG. 19B illustrates an enlarged subarea of FIG. 19A;

FIGS. 20A and 20B: sectional views of the connectors and the securing sleeve according to example 4 in a connected and released configuration, wherein FIG. 20B illustrates an enlarged subarea of FIG. 20A;

FIGS. 21A and 21B: the connectors and the securing sleeve according to example 4 in a separated configuration, wherein FIG. 21A shows a side view of the system and FIG. 21B shows a perspective view of the system;

FIGS. 23A and 23B: sectional views of the connectors and the securing sleeve according to example 5 in a connected and secured configuration, wherein FIG. 23B illustrates an enlarged subarea of FIG. 23A;

FIGS. 24A and 24B: sectional views of the connectors and the securing sleeve according to example 5 in a connected and released configuration, wherein FIG. 24B illustrates an enlarged subarea of FIG. 24A;

FIGS. 27A and 27B: a perspective illustration and a longitudinal section of an example of a securing sleeve for the system and blood pump system shown in FIGS. 25A through 25C;

Features that are the same or that correspond to one another have the same reference numbers.

DETAILED DESCRIPTION

Figures 4A, 4B:
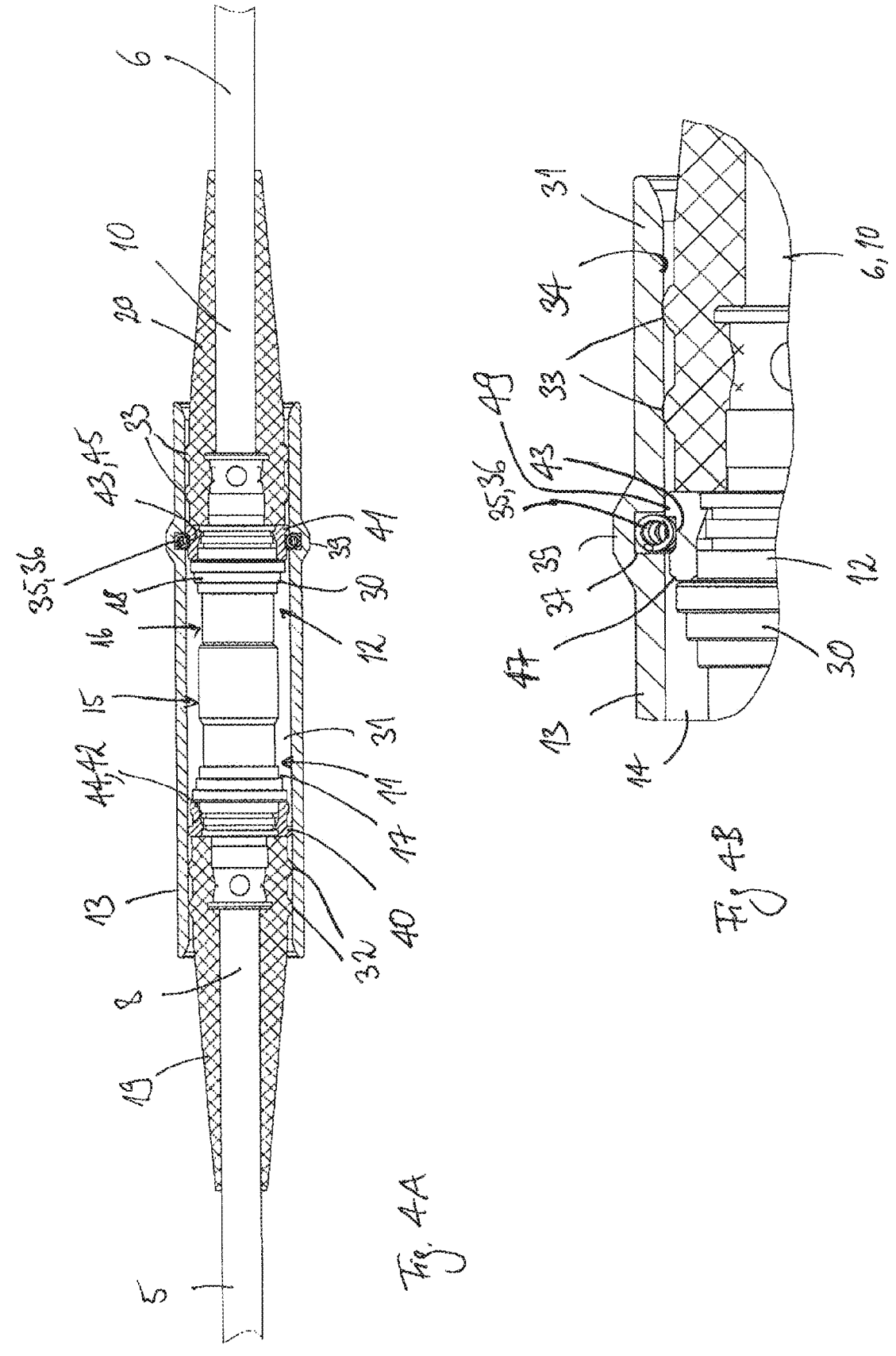

The present invention relates to a system for securing a releasable connection between two elements, in particular between two cables or between two hollow bodies, for example. The invention further relates to a blood pump system that comprises such a system.

In various areas of engineering it is necessary to secure releasable connections between two elements, for instance between two cables or between two hollow bodies. For example, one goal of securing such a connection can be to prevent unwanted release of the connection. Additionally or alternatively, it can be a goal of securing the connection to improve other security aspects of the connection. For example, it can be a goal to improve an electrical shielding or an electrical insulation of the connection and/or to provide reliable protection against accidental electrical contact. Additionally or alternatively, it can be a goal to protect one or both of the connected elements, for example from unwanted deformation or damage.

It is frequently important that it be possible to secure and release the existing connection as quickly as possible and as simply as possible. It can also be required that it be possible to secure and release the connection purely manually, that is, without the use of tools. Moreover, the probability of operator errors in securing and releasing the connection should be as small as possible. In addition, it can be another objective to simplify and accelerate the operation of the system when making and releasing the connection.

Making and securing a connection simply and quickly and unsecuring and releasing the connection simply and quickly is of great importance, for example, in the case of blood pump systems. An important application is, for example, the manual replacement, by the patient or by medically trained personnel, of a non-implanted controller for an implanted blood pump by a new non-implanted controller. This must involve first unsecuring and releasing the existing connection between the cable coming from the implanted blood pump and the cable coming from the controller to be replaced. Then, it is necessary to make and secure, in as short a time as possible, a new connection between the transcutaneous cable coming from the blood pump and the cable of the new controller. In blood pump systems (VAD systems), reliable securing of this connection (typically a plug-and-socket connection) is of the greatest importance, since an accidental or unwanted release of this connection can lead to the death of the patient.

Thus, it is a goal of this invention to suggest a system that makes it possible to secure and release a releasable connection between two elements as simply and quickly as possible. It should also suggest a corresponding blood pump system in which it is possible to secure and release a connection, for example between two cables to transfer control signals and sensor signals and to transfer energy to drive the blood pump, or a connection between two hollow bodies to carry blood as quickly and simply as possible.

This is accomplished, for example, by a system for securing a releasable connection between two elements and by a blood pump system that includes the system for securing the releasable connection. The system for securing the releasable connection can include: a first connector and a second connector, which is releasably connectable to the first connector; a securing sleeve configured to be moveable, if the first connector is connected to the second connector, by displacement of the securing sleeve, relative to the first connector and relative to the second connector, to a securing position in which the securing sleeve completely or at least partially receives the first connector and the second connector; and a latching device with at least one latching element, wherein the latching device is configured to produce a latching connection between the securing sleeve in the securing position and the first connector and/or the second connector connected to the first connector. Further developments and specific sample embodiments of the system and also of the blood pump system follow from the following description and the figures.

The suggested system for securing a releasable connection between two elements comprises a first connector and a second connector which is releasably connectable with the first connector. The system also comprises a securing sleeve, which is also referred to below as a sleeve for short. The securing sleeve is typically movably connected with the first and/or the second connector. If the first connector is connected with the second connector, the sleeve is movable into a securing position, for example by axial displacement of the securing sleeve relative to the first connector and the second connector. The two elements, also referred to below as the first element and the second element, whose releasable connection should be secured by the system, can be components of the system.

The blood pump system suggested here comprises the system suggested here for securing a releasable connection between two elements. The blood pump system also comprises an implantable or non-implantable blood pump and typically also comprises an implantable or non-implantable control device for the blood pump. The blood pump system also comprises, for example, a pump-side cable (for example, as a first element) that has a first cable end, which is connectable with the blood pump, and a second cable end. For example, the blood pump system also comprises a controller-side cable (for example, as a second element) with a first cable end that is connectable with the control device, and with a second cable end. The two cables can be configured, for example, to transfer control signals and sensor signals and/or to transfer energy to drive the blood pump. In this example, the first connector of the system can be solidly connected with the second cable end of the pump-side cable, and the second connector of the system can be solidly connected with the second cable end of the controller-side cable. In a typical embodiment, the blood pump is implantable and the control device is non-implantable. In this case, therefore, the control device is intended for extracorporeal use. The blood pump-side cable is then at least sectionally implantable and/or configured as a transcutaneous cable. In this case, the second end of the pump-side cable, the controller-side cable, as well as the connectors and the securing sleeve are typically designed for extracorporeal use.

Alternatively, the two elements to be connected can also be hollow bodies for carrying blood, such as, for example, a pump inlet or outlet, a connecting tube or connecting pipe, or a vascular prosthesis (graft). Such hollow bodies, which thus form a flow channel for a fluid, such as, for example, blood or another endogenous or exogenous fluid, are frequently also referred to as cannulas. Thus, the system can comprise, for example, an implantable or extracorporeal cannula arrangement, or be a part of such a cannula arrangement.

Accordingly, the blood pump system with such a system or with such a cannula arrangement as a first element can have a first such hollow body having a first end that is connected or connectable with the blood pump, and a second end. As a second element, the blood pump system can have a second such hollow body with a first end and a second end. Then the first connector of the system can be connectable or (solidly or releasably) connected with the second end of the first hollow body, and the second connector of the system can be connectable or (solidly or releasably) connected with the second end of the second hollow body. The two connectors are then typically configured to connect the two hollow bodies together in a fluid-tight manner, so that their flow channels form a continuous flow channel for the blood.

Various sample embodiments of the suggested system are described below. Since the suggested blood pump system can comprise these sample embodiments, these sample embodiments also simultaneously provide corresponding sample embodiments of the suggested blood pump system.

The terms radial, axial, and azimuthal are defined with respect to the longitudinal axis (central axis) of the respective part (connector, sleeve, element, etc.). The securing sleeve is displaceable, relative to the first connector and the second connector connected with it, into the securing position, preferably by manual displacement of the securing sleeve. This displacement is typically axial, i.e., parallel to the longitudinal axis of the securing sleeve and/or parallel to the longitudinal axes of the first connector and of the second connector. The longitudinal axes of the first connector and of the second connector and of the securing sleeve are typically arranged on a common line, if the two connectors are connected together. The axial displacement typically also takes place relative to the two (connected) elements. The mentioned securing position of the securing sleeve is defined relative to the first connector and relative to the second connector, typically at least by the axial position of the securing sleeve relative to the first connector and relative to the second connector, if the two connectors are connected together.

In the securing position, the securing sleeve completely or at least partly receives each of the first connector and the second connector, that is, completely or at least partly covers the first and second connector. The securing sleeve defines a hollow space (a lumen or a channel) that is suitably dimensioned for this purpose. Typically, the hollow space completely and continuously passes through the securing sleeve in the axial direction. As is explained in detail further below, when the securing sleeve is in the securing position, it typically completely receives at least the front ends (which possibly face one another) of the two connectors and preferably also locking elements, if they are present, of the connectors and/or control elements of the locking elements of the connectors.

In one embodiment, the securing sleeve is movable relative to the first connector and/or relative to the second connector into a holding position that is different from the securing position through displacement of the securing sleeve relative to the first connector and relative to the second connector. Preferably, both connectors are visible to the user if they are connected together and if the securing sleeve is in the holding position. Preferably, when the securing sleeve is in the holding position, it is arranged relative to the connectors in such a way that each of the two connectors is entirely or partly arranged outside of the securing sleeve, but at least the two front ends (which possibly face one another) of the two connectors are arranged outside of the securing sleeve, and therefore are visible. In many cases this makes it simpler for the user to connect the connectors together, especially when the connection of the connectors presupposes a specified azimuthal orientation of the connectors relative to one another.

The system typically comprises a latch device with at least one latch element. In addition, the latch device has at least one counter latch element that corresponds with the at least one latch element, this counter latch element being in the form of a receiver or support surface for the at least one latch element, for example. The latch device is configured to produce a latch connection between the securing sleeve and the first connector and/or between the securing sleeve and the second connector. Typically, the latch device is configured so that the latch connection is made or can be made when (and preferably only when) the securing sleeve is in the securing position relative to the first connector and relative to the second connector and when the first connector is also connected with the second connector. In one variant, this latch connection is only provided between the securing sleeve and the first connector. In a second variant, the latch connection is only provided between the securing sleeve and the second connector. In a third variant, the latch connection is provided between the securing sleeve on the one hand, and the first and the second connector on the other hand.

Additionally or alternatively, it can be provided that the latch device is configured so that a(nother) latch connection can be made between the securing sleeve and the first connector or the second connector if the securing sleeve is located, relative to the first connector or relative to the second connector, in the holding position that is different (defined relative to the first connector or relative to the second connector) from the securing position. The latch connection then stabilizes the securing sleeve in the holding position, in particular stabilizes it against unwanted displacements in the axial direction.

The mentioned latch connection of the securing sleeve in the securing position has the particular advantage that it can be made easily and quickly. Therefore, the sleeve can be fixed in the securing position very simply and quickly. Preferably, the latch device is configured so that the at least one latch element engages by itself if the sleeve is moved into the securing position by axial displacement. This typically does not require, or requires only slight (azimuthal) rotation of the sleeve with respect to the connectors, for example to achieve a correct (azimuthal) orientation of the latch elements (for example with respect to corresponding latch surfaces or counter latch elements), if required. However, such a rotation is typically less than 180°, preferably less than 90°. In particular, this allows the suggested latch connection to be made more quickly than, for example, a connection by means of a thread, which typically would require multiple complete turns of the securing sleeve with respect to the connectors.

The latch connection can stabilize the securing sleeve in the securing position, for example against unwanted displacements in the axial direction. After the latch connection is released, or due to its release, it is possible to move the sleeve back out of the securing position to release the connection of the connectors. Releasing the latch connection of the sleeve with the first and/or second connector can require, for example, displacement of the sleeve with a predefined axial minimum displacement force, rotation of the sleeve about its longitudinal axis, and/or a radial compression of the sleeve in a predefined direction, as is explained in detail below.

Typically, the securing sleeve is configured in such a way, and is arranged relative to the first and/or second connector in such a way that at any time it receives at least one axial section of the first connector and/or an axial section of the second connector. Typically this is the case at least when the securing sleeve is in the securing position, but typically also when it is outside the securing position, for example in the holding position of the securing sleeve. For example, the securing sleeve is secured to the first connector by means of an axial stop that is arranged on the first connector or on the first element. In an alternative variant, the securing sleeve is secured to the second connector by means of an axial stop that is arranged on the second connector or on the second element. The stop can be arranged in such a way, for example, that starting from the securing position, for example, the sleeve can be axially displaced relative to the respective connector only as far as the mentioned axial stop. This makes it possible, for example, to avoid an unwanted separation of the sleeve from the first or the second connector.

Each of the two mentioned elements can be, for example, a cable or an end of a cable. Each of the cables can comprise an outer sheath, defining at least one lumen that extends along the outer sheath, and at least one conductor that extends along the cable and within the outer sheath, if it is present (through at least one lumen). The outer sheath is typically made of an electrically insulating material. Each of the conductors can be configured as an electrical conductor to transfer electrical energy and/or electrical signals or as an optical conductor to transfer optical signals. Then, the cables can be, for example, cables for a blood pump system, for example for the blood pump system suggested here. Such cables are frequently also referred to as the "driveline" of the blood pump system.

As was already described above, each of the two mentioned elements can also be, for example, a hollow body, such as, for example, a tube, a pipe, an inlet nozzle or outlet nozzle of an implantable or non-implantable pump, in particular a blood pump, or an implantable vascular prosthesis (a so-called graft), or an end of such a hollow body. In particular, the hollow bodies can be configured to carry a fluid, such as, for example, blood, as in the case of the blood pump system suggested here.

One or both of the elements can be implantable, and for this purpose can entirely consist, for example, of a biocompatible material, or at least have areas that consist of such a material, or can be completely coated with such a material, or can at least have areas that are coated with such a material. In the same way, the two connectors can be implantable, and for this purpose can entirely consist, for example, of a biocompatible material, or at least have areas that consist of such a material, or can be completely coated with such a material, or at least have areas that are coated with such a material. The securing sleeve can also be implantable, and for this purpose can entirely consist, for example, of a biocompatible material, or at least have areas that consist of such a material, or can be completely coated with such a material, or at least have areas that are coated with such a material. Examples of possible biocompatible materials are biocompatible polymers such as, for instance, silicone, and biocompatible metal materials, such as, for example, titanium and nitinol.

The releasable connection between the two elements is completely or at least partly produced by the releasable connection between the first connector and the second connector. This is typically accomplished by solidly connecting the first connector with one of the two elements, which is referred to below as the first element. The second connector is also typically solidly connected with other one of the two elements, which is referred to below as the second element.

The first connector and the second connector each typically comprises a housing, which is typically made of a metal material, for example brass, aluminum, or (stainless) steel. This makes it possible to achieve, for example, high stability and durability of the connectors. One or both of the connectors can (each) comprise a handling part, which forms an outer (preferably structured) handling surface, to improve the manual handling of the connector. The handling part is typically solidly connected with the housing of the respective (first or second) connector. The handling part can also be made of a metal material, for example brass, aluminum, or (stainless) steel, or of a polymer, such as, for instance silicone, POM, or PUR.

Each of the two connectors comprises the already mentioned front end and a back end. In the connected state, the front end of the first connector typically points toward the second element and/or toward the second connector and the front end of the second connector also typically points toward the first element and/or toward the first connector. Typically, each of the connectors is connected (typically solidly or releasably) with the first or the second element through its back end. Typically, at least areas of the two connectors overlap one another in the axial direction when they are connected with one another.

The two connectors typically have a structure that is as compact as possible and in particular an external cross section that is as small as possible, for example a round, preferably circular external cross section (i.e., an external cross section that is rotationally symmetric with respect to the longitudinal axis of the first or second connector).

For example, the first connector and the second connector can form a plug-and-socket connector. That is, the connection between the first connector and the second connector is then a plug-and-socket connection, which can be made by pushing the connectors together or into one another in the axial direction. For example, the first connector can be in the form of a plug and the second connector can be in the form of a socket (if the connector is, e.g., part of a housing, e.g., a controller) or in the form of a coupling (if the connector is solidly connected, for example with a cable). Alternatively, the first connector can be configured, for example, in the form of a socket or a coupling, and the second connector in the form of a plug. The connector configured in the form of a plug has, at its front end, a coupling element that can be configured, for example, in the form of a pin or sleeve. The connector that is configured in the form of a socket or coupling has, at its front end, a receiving part for the coupling element of the plug. The receiving part can be configured, for example, in the form of a sleeve. If the connectors that are configured in this way, for example, are connected together, the coupling element is typically received in a receiving area defined by the receiving part.

Especially if both elements are configured as cables, the connectors can have corresponding contact elements that are configured to transfer electrical and/or optical signals and that are arranged on the first and second connector so that they are in contact with one another when the two connectors are connected with one another. For example, each of the contact elements can be connected with one of the above-described conductors of the respective cable. The contact elements can be arranged, for example, in the coupling element of the connector configured as a plug and in the receiving part of the connector configured as a socket or a coupling.

The releasable connection between the two connectors is typically a mechanical connection. Typically, this connection can be made and (nondestructively) released again practically as often as desired. Preferably, the connection between the connectors is stable with respect to axial tensile load; this is accomplished, for example, by locking the connection by means of a locking device of the connectors. Preferably, the connectors or the locking device are self-locking. For example, the first connector and/or the second connectors can have at least one locking element that can, for example, be configured as a latch element or a can have a latch element. The respective latch element can be provided, for example, by a latch arm that can have, for example, a latch tooth that projects radially inward or outward. In addition, the first and/or the second connector can have at least one counter locking element corresponding with the locking element, for example in the form of a receiver or support surface for the at least one locking element. The at least one locking element is preferably made of a metal material. The counter locking element is typically made of a plastic or of a metal material and is shaped, for example, as a depression in the housing of the first or second connector.

The locking mechanism typically has a (manually controllable) control element that is movably connected (for example, connected so that it is axially displaceable) with the housing of the first (alternatively the second) connector. The at least one locking element is movably connected, for example, with the control element (first variant) or alternatively with the housing (second variant) of the first (alternatively the second) connector, for example through an articulation. The articulation (which is preferably made of a metal material) can be, for example, an elastic area of the control element or an elastic element that is solidly connected with the respective control element (first variant). Alternatively (second variant), the articulation can be an area of the housing of the first (alternatively second) connector or an elastic element that is solidly connected with it (second variant).

For example, it is possible that the at least one locking element is movable (e.g., by means of the articulation) between a predefined locking position and a predefined unlocking position, the connection between the two connectors preferably being (nondestructively) releasable only when the at least one locking element is in the unlocking position. For example, the at least one locking element is movable by a (typically manual) manipulation of the at least one locking element or by a (typically manual) manipulation of a movable control element of the respective connector (as in the second variant), for example from the locking position into the unlocking position, to unlock the connection. Alternatively, it is also possible (for example, in the first variant), that the at least one locking element is only movable, for example from the locking position into the unlocking position, when the control element is (preferably manually) manipulated, and is otherwise not movable or blocked, for example by the control element or by a blocking element, which can be solidly connected, for example, with the housing of the first (alternatively the second) connector.

Typically (for example, in the first variant), the at least one locking element is moved into the locking position or kept in the locking position by the blocking element pressing the locking element into a constrained position (locked position). This automatic locking can, for example, allow the cable of the plug to be pulled, while the coupling (socket) is solidly held. The result is that the locking element, which is fastened through an articulation with the control element that is freely movable relative to the plug housing (variant 1), is kept in the locking position by typically conical, pairs of surfaces sliding one on another (one conical surface sliding on the locking element, and one conical surface sliding on the blocking element). The conical surfaces have the effect that the greater the tensile force on the cable, the more the conical surfaces press against one another. The result is that the axial tensile forces are radially deflected as a function of the cone angle, so that greater forces produce greater locking forces (pressing between the pairs of conical surfaces). When the control element is manipulated, it is then typically impossible to move the control element into the unlocking position. For example, the control element can be movable between a blocked position and an unblocked position by (preferably manual) manipulation, the locking element only being movable from the locking position into the unlocking position when the control element is in the unblocked position.

Preferably, the at least one locking element or, if present, the at least one control element for the at least one locking element, is arranged in such a way that it is (manually) inaccessible (and thus also not manually manipulable) from outside if the two connectors are connected with one another and if the sleeve is in the securing position. The at least one locking element or the associated control element are then arranged in the hollow space of the sleeve. This means that the sleeve protects the connection of the connectors from unwanted unlocking. Preferably, if the two connectors are connected with one another, the at least one locking element or the control element is only (manually) accessible and manipulable from outside when the sleeve has been moved sufficiently far out of the securing position, for example into the above-described holding position. The fact that the sleeve has engaged into the securing position prevents unwanted movement of the sleeve out of the securing position and unwanted unlocking of the connection of the connectors, which is, in principle, made possible as a result, or at least makes this more difficult. This is especially important in the case of percutaneous VAD drivelines. Here the fundamental goal is for the connector to have as small a diameter as possible (important in operations or implantations) and a small weight and a short length (important for users in everyday life). Therefore, the connectors that are typically commercially available and the forces required to manipulate them are relatively small. However, as a rule small manipulation forces increase the risk of unwanted opening of the connection.

Preferably, the at least one locking element and/or, if present, the respective articulation of the locking element or of the control element, is configured so that, for example, a corresponding pretensioning of the locking element or of the articulation causes the locking element to be in the locking position or to move into this locking position by itself, if no manipulation force or other external force acts on the locking element or on the control element. This effect can also be produced, for example, by a correspondingly configured spring element of the respective connector, this spring element being connected, for example, with the locking element and the housing of the connector. This allows the connectors to be self-locking, for example.

As was already described above, the first or second connector can have at least one corresponding counter locking element for the at least one locking element, for instance in the form of a receiver, support surface, or depression in the housing of the respective connector. In this case, the at least one locking element is typically entirely or at least partly interlocked with this counter locking element if the locking element is in the locking position and the two connectors are connected with one another. The at least one locking element and the at least one corresponding counter locking element are preferably configured so that the connection of the connectors is locked if the at least one locking element is in the locking position, and can only be (nondestructively) released by (typically manual) unlocking of the connection, that is by moving the at least one locking element into the unlocking position, in which the at least one locking element is not interlocked with the respective counter locking element. As described above, this can presuppose manipulation of a control element. The release is then typically accomplished by pulling the connectors apart in the axial direction.

For example, the connection between the connectors can be a latch connection. For this purpose, the first connector and/or the second connector can have latch elements or corresponding counter latch elements, for example in the form of receivers or support surfaces for the latch elements. The latch elements of the first and/or second connector are typically different from the at least one latch element of the above-mentioned latch device, which makes the latch connection between the securing sleeve and the first and/or second connector. For example, the above-described locking elements can be configured as latch elements and, accordingly, the mentioned counter locking elements can be configured as corresponding counter latch elements.

Possible examples of lockable connectors are so-called push-pull connectors, that is, connectors that have a push-pull mechanism for locking, such as described, for example, in EP 2 287 974 B1. Other possible variants of push-pull connectors are offered, for example, by the manufacturers Fischer Connectors and Lemo.

Especially in the case when the two elements are hollow bodies, such as, for example, cannulas, the two connectors can be configured to connect the two elements by means of a non-positive and/or frictional engagement. If the two hollow bodies form flow channels, such as, for instance for blood or other fluids, the two connectors are, as a rule, configured to connect the two hollow bodies together in a fluid-tight manner, so that the two hollow bodies form a continuous flow channel.

For example, the first connector can be arranged at least partly within the flow channel of the of the first element or form a part of the flow channel of the first element. If the two elements are connected with one another, the first connector can also be arranged, for example, partly within the flow channel of the second element. For example, at the second end of the first element the first connector can be partly pushed into the flow channel of the first element and partly project out of it. The first connector can, for example, be solidly connected with the first element and, for example, be made as a single piece with the first element. For example, the first connector can be formed by an axial end section of the first element at its second end, at which the first element can have, for example, a reduced outside diameter.

If both elements are connected with one another, the first connector is then typically pushed into the flow channel of the second element or hollow body. That is, in these cases the first connector thus forms a part of the flow channel of the system.

The first connector can, for example, be configured as a tubular element, such as, for example, a (centering) sleeve.

The tubular element can, for example, be dimensioned so that it can be pushed into the first and/or the second hollow body of the first or second element, for example into a flow channel of the first or second hollow body.

The second connector can be configured as a corresponding clamping element, for example as a hose clamp or a split sleeve. The second connector is then typically dimensioned so that it can surround the second end of the second element and, inserted into it, the front end of the first connector, to introduce a clamping force onto these parts. To accomplish this, it can be provided that the second connector can be put into a tensioned state to exert a clamping force that acts (for example, radially inward or alternatively outward) on the second element, and thus to make a fluid-tight clamping connection between the second element and the first connector. For example, to make and/or to stabilize the tensioned state, the second connector can have a screw-type connection with a tightening screw and a corresponding threaded part. Alternatively, the second connector could also comprise a latch-type connection with corresponding latch elements or an elastic spring element.

Of course it is also possible for the roles played by the first and second connectors to be the reverse of those described above.

For example, the first or second connector configured in the form of a tubular element can have a counter latch element of the latch device, for example a latch surface, in particular an annular groove. Additionally or alternatively, the second or first connector configured as a clamping element (e.g., the hose clamp), can also have a counter latch element of the latch device, for example a latch surface, in particular an annular groove.

The at least one latch element of the latch device can comprise precisely one latch element, or also more than one latch element. For better readability, the following discussion uses the terms "a latch element" or "the latch element", which should be understood to mean "at least one latch element of the at least one latch element of the latch device" or "the at least one latch element of the at least one latch element of the latch device". Therefore, if multiple latch elements are present, the statements can always refer either only to a single latch element of the latch device or also to multiple or to all latch elements of the latch device.

The latch device can comprise at least one counter latch element. For example, a corresponding counter latch element can be provided for each latch element. If one of the described latch connections is made by means of the latch device, then for example each of the one or more of the at least one latch element can be interlocked with a counter latch element. For example, the latch element can reach behind the respective counter latch element. For example, the latch elements can be configured to be movable, flexible, and/or elastic, while the counter latch elements can, for example, be configured to be immovable and rigid. A reverse configuration is also possible.

For example, a latch element of the latch device can be configured,
   to engage on a surface of the first connector or
   to engage on a surface of the second connector or
   to engage on a surface of the securing sleeve,
if the securing sleeve is in the securing position, or, additionally or alternatively, if the securing sleeve is in the holding position. In these sample embodiments, the mentioned surfaces can be formed, for example, by the above-mentioned counter latch elements, for example in the form of receiving areas or latch surfaces for the respective latch element. Such counter latch elements can also be formed, for example, by a suitable shape of the outer contour of the first or second connector or by a suitable shape of the inner contour of the sleeve. The respective counter latch element can be formed, for example, by an undercut, a groove, a channel, a depression, a ridge, a bulge, or something similar on the respective surface. It is possible for the surface or the counter latch element to be formed by the housing of the connector or another (for example, annular) element such as, for example a handling part that is solidly connected with the respective connector or its housing or with the sleeve.

For example, the latch element and the respective counter latch element can be shaped so that the securing sleeve is movable out of the securing position or the holding position by axial displacement of the securing sleeve, if an axial displacement force acting on the securing sleeve exceeds a predefined threshold. To accomplish this, for example, the latch element or the respective counter latch element can (each) have an angled ascending surface that is bent at an angle so that the interlocking of the latch element and the counter latch element is released if the securing sleeve is pushed, with this displacement force, out of the securing position or the holding position.

For example, a latch element, multiple latch elements, or every latch element of the latch device can be a component of the first connector or a component of the second connector or a component of the securing sleeve, and/or can be solidly connected with the first connector, the second connector, or the securing sleeve, so that the respective latch element is not released from here if the securing sleeve is moved out of the securing position (or the holding position).

The latch device can comprise, for example, a support for the latch element or the latch elements. The support can be configured, for example, in the form of a sleeve. The support can be a subarea of the securing sleeve or an element that is integrated into the securing sleeve. For example, the solid connection between the respective latch element and the first connector, the second connector, or the securing sleeve can be made by cementing.

The securing sleeve and the at least one latch element that is solidly connected with it can also be formed by an integral injection-molded part, for example by a 2K injection-molded part, as is described further below.

A latch element, multiple latch elements, or every latch element of the latch device can, for example, be movable and/or be entirely elastic, or at least parts of it/them can be elastic. The respective latch element can be formed, for example, of a metal or polymer material.

For example, a latch element, multiple latch elements, or every latch element of the latch device can be configured as an elastic ring element. For example, each latch element(s) can configured as a coil spring that is wound in the shape of a ring or as an axial circlip or as an O-ring. Such an elastic ring element typically completely (azimuthally) encircles the longitudinal axis of the securing sleeve, the first connector, or the second connector. For example, at least one (closed) annular groove corresponding with this latch element can be provided on the inside surface of the sleeve, on the outer surface of the first connector, or on the outer surface of the second connector, this groove typically completely (azimuthally) encircling the longitudinal axis of the securing sleeve, the first connector, or the second connector. For example, the elastic ring element can be arranged partly within such an annular groove on the inner surface of the sleeve and be permanently fastened there, for example by residual stresses, and enter into a corresponding annular groove on the outer surface of the first or second connector, if the sleeve is in the securing position (or in the holding position). Of course a reverse configuration is also possible. The coil spring can be, for example, a coil spring of the type described in EP 0890758 A2 ("coiled spring") or of the type described in EP 1468192 B1 ("helical spring").

Furthermore, one latch element, multiple latch elements, or every latch element of the latch device can have, for example, a bulge or a projection, which projects radially inward starting from an inner surface of the securing sleeve. Conversely, it is possible for one latch element, multiple latch elements, or every latch element of the latch device to have a bulge or a projection, which projects radially outward starting from an outer surface of the first or second connector.

Each mentioned bulge or projection can be configured, for example, as a little bump, a rib, or a ridge.

The securing sleeve can comprise a sleeve-shaped main body. The mentioned bulge or projection, which, for example, projects radially inward from the inside surface of the main body, can be softer than the sleeve-shaped main body of the securing sleeve. For example, the main body and the bulge or projection can be formed of different materials that have different strengths. For example, the sleeve can be a 2K injection-molded part.

One sample embodiment provides that the latch device have two or more latch elements. Each of at least two of these at least two latch elements has a bulge that projects radially inward from an inner surface of the securing sleeve. The securing sleeve has an (untensioned) initial state that it assumes, for example, when no external force, in particular no radial compressive force, acts on it. When the securing sleeve is in the initial state, the two bulges assume a first distance from one another. The first radial distance is defined in a first radial direction and is dimensioned so that the two bulges engage or are engaged in the surface of the first connector or the surface of the second connector if the securing sleeve is in the initial state and is in the securing position relative to the first connector and the second connector connected with the first connector. For example, each of the two bulges then enters into a corresponding receiver on the surface of the first or second connector or reaches behind corresponding bulges on the surface of the first or second connector.

In this example, the securing sleeve is deformable into a (tensioned) intermediate state by a radial compressive force (which has a predetermined strength) that acts on the securing sleeve in a second radial direction that is different from the first radial direction. This compressive force can be produced, for example, by manual compression of the sleeve. To accomplish this, the sleeve can have, for example, correspondingly marked areas on its outer surface. The mentioned deformation of the sleeve is preferably elastic, so that the securing sleeve deforms back into the initial state by itself, as soon as the radial compressive force is no longer acting on it.

When the securing sleeve is in the intermediate state, the two bulges assume a second distance from one another defined in the first radial direction. The second distance is greater than the first distance and is dimensioned so that the two bulges are not engaged in the surface of the first connector and/or the surface of the second connector (that is, they do not then, for example, enter into the above-mentioned receivers or do not reach behind the above-mentioned bulges), if the securing sleeve is in its intermediate state and is simultaneously in the (axially defined) securing position relative to the first connector and the second connector connected with the first connector. That is, when the sleeve is in the securing position it does not engage if it is in its intermediate state, since the radial distance of the two bulges from the surface of the first or second connector is too great for this to happen.

As long as the sleeve is in the intermediate state, for example by continuous compression, the sleeve can be axially pushed relative to the first and second connector in the securing position, without a latch connection existing or being made between the sleeve and the connectors. As soon as the sleeve is in the securing position and in this position returns (by itself) to its initial state, for instance due to the compression ending, the bulges of the two mentioned latch elements engage on the surface of the first or the second connector. To release this latch connection, the sleeve can be put into the intermediate state and kept there by compression, and in the intermediate state it can be moved back out of the securing position by axial displacement.

The securing sleeve or its sleeve-shaped main body can have a cross section, in particular an inner contour, whose shape, for example in the initial state, is oval (or alternatively circular, i.e., rotationally symmetric with respect to the longitudinal axis), and in the intermediate state for example is circular (alternatively oval). Preferably, a smallest inside diameter of the sleeve in the intermediate state is greater than a largest outside diameter of the first connector and/or than a largest outside diameter of the second connector. Typically the first connector and/or the second connector have an (outer) cross section, that is an outer contour, that is circular (i.e., rotationally symmetric with respect to the longitudinal axis).

For example, the latch device can have at least one flexible latch arm. The latch arm has, for example, a latch element of the latch device in the form of a bulge that projects radially inward. This bulge is also referred to below as a latch tooth. The latch arm typically extends in the axial direction, that is, essentially parallel to the longitudinal axis of the sleeve. Typically the latch arm is solidly connected with the securing sleeve.

For example, the surface of the first connector or the surface of the second connector can have at least one step that forms a latch surface for the at least one latch arm. If the sleeve is in the securing position, the latch tooth of the latch arm reaches behind the step or the latch surface. The step or the latch surface can be formed, for example, by a (terminal) collar or a (terminal) ridge of the connector, or by a groove or a channel. If the sleeve is in the securing position and the latch tooth is engaged in the surface of the first or second connector, then the latch connection has been made between the securing sleeve and the first or second connector.

The first connector and/or the second connector can have at least one unlocking ascending surface, which is arranged, for example, on the (outer) surface of the connector and which borders, for example, the latch surface formed by the step. Typically, the unlocking ascending surface is arranged on a back surface of the step. If the sleeve is in the securing position, when the sleeve undergoes (azimuthal) rotation the latch arms slide over the unlocking ascending surfaces and are radially spread apart. This typically involves the radially inward directed bulges or latch teeth of the latch arms sliding over the unlocking ascending surfaces.

The latch arm typically has an ascending surface that is arranged on a front surface of the latch tooth, and a support surface that is arranged on a back surface of the latch tooth, this back surface facing away from the front surface. Generally speaking, the front surface of the latch tooth faces the (typically cantilevered) head end of the latch arm, and the support surface of the latch tooth faces the (typically bordering the sleeve or a support) foot end of the latch arm.

The support surface, which preferably is planar, can be bent at an angle with respect to a reference plane that is perpendicular to the longitudinal axis of the securing sleeve. Preferably the angle that is included between the support surface and the reference plane lies between 30° and 60°. Additionally or alternatively, the ascending surface, which is preferably planar, can be bent at an angle with respect to the mentioned reference plane. Preferably the angle that is included between the ascending surface and the reference plane lies between 30° and 60°. The choice of the angle of the ascending surface can predetermine, for example, a (manual) manipulation force for the engagement of the latch arm and in this way define, for example, the (manual) manipulation force that must be applied to push the sleeve into the securing position and make the latch connection between the sleeve and the first and/or second connector. The choice of the angle of the support surface can correspondingly predetermine a manipulation force for disengagement of the latch arm and in this way define, for example, the (manual) manipulation force that is required to push the sleeve out of the securing position and release the latch connection between the sleeve and the first and/or second connector.

Moreover, the system can have a flexibly shaped protective element for the first element and/or for the second element. Typically, the protective element defines a channel for the first and/or second element, that is a channel into which at least sections of the first and/or second element can be received, for example when the securing sleeve is in the securing position. The channel of the protective element forms, for example, a part or a (typically coaxial) continuation of the hollow space of the securing sleeve.

The protective element can be configured, for example, in the form of anti-kink protection and/or cutting protection for the first or second element. This can be advantageous especially when the respective element is configured as a cannula, e.g., a vascular prosthesis made of a graft material. The protective element is typically configured to be mechanically more stable than the respective element to be protected.

Typically, the protective element is solidly connected with the securing sleeve. It can also be configured as a part of the securing sleeve. For example, the securing sleeve can have a main body that is typically configured to be sleeve-shaped and partly or completely forms the mentioned hollow space of the securing sleeve. The main body is preferably configured to be stable (i.e., rigid and fixed) and can be solidly or detachably connected with the protective element. Typically, the main body has at least one latch element of the latch device.

The securing sleeve or its main body can be connected with the protective element, for example, by material bonding, for example with a front end of the protective element or for example with a frontmost of the segments described further below (if the protective element is built in segments).

The protective element can be configured as the protective element described in European patent application EP 16 16 4527.0. That is, for example, the protective element can comprise multiple segments, which are arranged next to one another in a sequence. Each of the segments then defines a partial section of the channel of the protective element.

The segments can be entirely or at least partly formed of an elastically deformable polymer, for example a silicone, a silicone elastomer, or a polyurethane. The polymer (e.g., soft silicone) can have a Shore A hardness of 30-90, for example. The segments can be injection-molded parts, for example.

The protective element can have at least one connection element, which connects the segments with one another. The connection element(s) can be connected with the segments by material bonding, for example.

The at least one connection element can be configured as at least one cable-shaped element, for example with round or flat cross section. The at least one cable-shaped element can be directly connected with two or with more than two segments, or with every one of the segments by material bonding, for example. The at least one cable-shaped element can comprise two or more such cable-shaped elements, the cable-shaped elements being arranged spaced apart from one another in a peripheral direction around the protective element.

The segments can be connected with one another in such a way that the segments are movable relative to one another. For example, the segments can be rotatable relative to one another about a longitudinal axis of the channel, for example by at least 3° or by at least 5°.

If the protective element has the described segmented structure, it can be shortened by separating from one another two segments that are adjacent in the sequence, for example by cutting through at least one or each connection element of the connection elements of the protective element that connects the two adjacent segments with one another, this cutting being performed by means of a manually guided cutting instrument, for example by means of a scalpel.

Other possible sample embodiments of the protective element can be found in European patent application EP 16 16 4527.0.

In sample embodiments in which the securing sleeve has such a protective element, the securing sleeve preferably has a latch element of the latch device. This latch element can be configured as an elastic ring element which encircles the hollow space of the securing sleeve in the shape of a ring. The latch element is preferably configured as a coil spring that is wound in the shape of a ring or as an axial circlip or as an O-ring.

For example, the above-mentioned (typically sleeve-shaped) main body of the securing sleeve can be made of titanium or of another metal or of a polymer. The main body can, for example, be cemented with the protective element. The main body can have, for example, another sleeve screwed into it, made of polyoxymethylene (POM) or another polymer, for example. This sleeve can have, on an inside surface, an annular groove to receive the above-mentioned elastic ring element (e.g., a coil spring that is wound in the shape of a ring).

Alternatively, the (sleeve-shaped) main body of the securing sleeve can also be made of a polymer that is preferably relatively hard (preferably Shore B-C) in comparison with the protective element, for example a correspondingly hard silicone. The annular groove of the elastic ring element can also be arranged, for example, directly on the (sleeve-shaped) main body or on its inner surface. The protective element can be cemented with this main body.

When the elastic ring element is in its initial shape (with no force applied to it), it can have, for example, an elliptical cross section. For example, the elastic ring element can be a coil spring that is wound in the shape of a ring of the manufacturer Bal Seal Engineering, Inc.

As the counter latch element or latch surface for the elastic ring element, the first connector or the second connector can have a corresponding annular groove, for example if the first connector or the second connector are configured as a tubular element or as a clamping element, as has already been described above.

The protective element can advantageously be pushed, together with the securing sleeve, over the respective element, for example, a cannula, and this can be done quickly and securely without damaging the element, that is, the cannula. In the securing position, the latch connection between the securing sleeve and the first or second connector typically simultaneously also fixes in place the protective element. Preferably, for example using the described elastic ring element as latch element, it is possible for a sufficiently large axial displacement force to make or release the latch connection, without this requiring rotation. In addition, it allows a very compact design.

Accordingly, the system suggested here can also be configured as the cannula arrangement described in European patent application EP 16 16 4527.0, be part of such a cannula arrangement, or comprise such a cannula arrangement. Furthermore, the blood pump system suggested here can be configured as the blood pump system described in European patent application EP 16 16 4527.0.

The suggested system and the suggested blood pump system are explained in detail below on the basis of FIGS. 1 through 29B, which schematically illustrate special sample embodiments of the system, the blood pump system, or individual components of them.

Each of FIGS. 1A through 1C shows a schematic representation of a system 1 for securing a releasable connection between two elements of the type suggested here as a component of a blood pump system 2 of the type suggested here.

The blood pump system 2 shown in FIGS. 1A through 1C also comprises an implantable blood pump 3 and an extra-corporeal (non-implantable) control device 4 for the blood pump 3. The blood pump system 2 comprises a first element 5 in the form of a pump-side cable with a first end 7 that is connectable with the blood pump 3, and with a second end 8. The blood pump system 2 also comprises a second element 6 in the form of a controller-side cable with a first end 9 that is connectable with the control device 4 and with a second end 10. The control device 4 is set up to send, through the two elements (cables) 5 and 6, electrical and/or optical signals to the blood pump 3, or to receive such signals from it. To accomplish this, the cables can comprise electrical and/or optical conductors, each of which extends along the respective cable. Each of the cables typically comprises an outer sheath that defines one or more lumen(s) for the conductors. The outer sheaths are typically made of an electrically insulating material.

The system 1 is set up to connect the two elements (cables) 5 and 6 with one another in a detachable manner in order to allow signal transfer between blood pump 3 and control device 4. To accomplish this, the system 1 comprises a first connector 11 and a second connector 12 that is detachably connectable with the first connector 11. In FIGS. 1A and 1B, the two connectors 11, 12 are connected with one another, and in FIG. 1C they are separated from one another. The first connector 11 of the system 1 is solidly connected with the second end 8 of the first element 5 (pump-side cable). The second connector 12 is solidly connected with the second end 10 of the second element 12 (controller-side cable).

Areas of the first element 11 (blood pump-side cable) are implantable and configured as a transcutaneous cable. To accomplish this, the first element 11, in particular the outer sheath of the first element 11, can entirely consist of a biocompatible material, or at least areas of it can consist of a biocompatible material, or can be completely coated with such a material, or at least areas of it can be coated with such a material. Examples of possible biocompatible materials are biocompatible polymers such as, for instance, silicone.

The system 1 also comprises a securing sleeve 13 or sleeve 13. The securing sleeve 13 is displaceably connected with the first connector 11. If the first connector 11 is connected with the second connector 12, as is shown in FIG. 1A, the sleeve 3 is movable into a securing position by manual axial displacement of the securing sleeve 13 relative to the first connector 11 and the second connector 12. The securing position is defined relative to the first connector 11 and relative to the second connector 12 by the axial position of the securing sleeve relative to the first connector 11 and relative to the second connector 12 when the two connectors 11, 12 are connected with one another.

In this example, the second end 8 of the first element 11, the second element 12 (controller-side cable), and the connectors 11, 12 and the securing sleeve 13 of the system 1 are designed for extracorporeal use.

In an alternative sample embodiment of the system 1 and the blood pump system, the two elements 11, 12 of the blood pump system 2 that are to be connected could also be hollow bodies to carry blood. For example, the first element 5 could be a pump outlet of the blood pump 3 and the second element 6 could be a vascular prosthesis, which is connected, for example, with a blood vessel, for example an aorta or a vein of the patient. The connectors 11, 12 can then also be configured to carry blood and be implantable. Such a sample embodiment is described in detail further below on the basis of FIGS. 26A through 29B.

As is shown in FIG. 1A, when the securing sleeve 13 is in the securing position, it partly receives each of the first connector 11 and the second connector 12, and thus partly covers the first and second connectors 11, 12. For this purpose, the securing sleeve 13 defines a hollow space 14, which completely and continuously passes through the securing sleeve 14 in the axial direction. In particular, when the securing sleeve 13 is in the securing position, it completely receives facing front ends 15, 16 of the two connectors 11, 12 and also locking elements, if they are present, of the connectors and/or control elements of the locking elements of the connectors.

The securing sleeve 13 is movable relative to the first connector 11 and/or relative to the second connector into a holding position that is different from the securing position by manual displacement of the securing sleeve 13 relative to the first connector 11 and/or relative to the second connector 12, as is shown, for example, in FIGS. 1B and 1C. As is shown in FIG. 1B, both connectors 11, 12 are visible to the user if they are connected together and if the securing sleeve 13 is in the holding position. Preferably, when the securing sleeve 13 is in the holding position, it is arranged relative to the connectors 11, 12 in such a way that each of the two connectors 11, 12 is entirely or partly arranged outside of the securing sleeve, but at least the two facing front ends 15, 16 of the two connectors 11, 12 are arranged outside of the securing sleeve, and therefore are visible. This makes it simpler for the user to connect the connectors together, especially when the connection of the connectors 11, 12 must maintain a specified azimuthal orientation of the connectors relative to one another. For this purpose, the connectors 11, 12 can have, for example, markings arranged on them, which make it possible to see a correct orientation of the connectors 11, 12 to one another if the securing sleeve 13 is in the holding position (see, for example, markings 50, 51 in FIG. 5 or correspondingly labeled markings in the other examples).

The example shown in FIGS. 1A through 1C shows a displacement of the sleeve 13 out of the securing position in the direction of the first element 5, that is, in the direction of the blood pump 3, so that the holding position is arranged on the side of the blood pump 3. However, conversely it would also be possible to provide that the sleeve 13 is displaced out of the securing position in the direction of the second element 5, that is in the direction of the control device 4. That is, the sleeve 13 can be, for example, a component of the first element 5, that is, of the first connector 11, or of the second element 6, that is, of the second connector 12.

For example, the sleeve 12 can be connected (such that it cannot be lost) with the first element 5 or the first connector 12 (alternatively with the second element 6 or the second connector 12). In this case, in the state of the system 1 shown in FIG. 1C (that is, if the connectors 11, 12 are separated from one another) the sleeve 13 cannot be removed from the first connector 11 over the latter's front end 15, and be separated in this way from the first connector 11. However, alternatively it can also be provided that the sleeve 13 can be removed from the first connector 12 over the latter's front end 15 and be separated from the connector 11. Then, the sleeve 13 can typically also (if the connectors are separated from one another) be pushed back on over the front end 15 of the first connector 11 (alternatively over the front end 16 of the second connector 12), to restore the state shown in FIG. 1C. The system 1 also comprises a latch device with at least one latch element (not shown in FIGS. 1A through 1C). The latch device or the at least one latch element is configured to create a latch connection between the securing sleeve 13 and the first connector 11 and/or between the securing sleeve 13 the second connector 12, if the securing sleeve is in the securing position relative to the first connector 11 and relative to the second connector 12, or if it is in the holding position relative to the first connector 11.

The figures below show five different sample embodiments of the system 1 or of components of the system 1.

Figures 5, 6A:
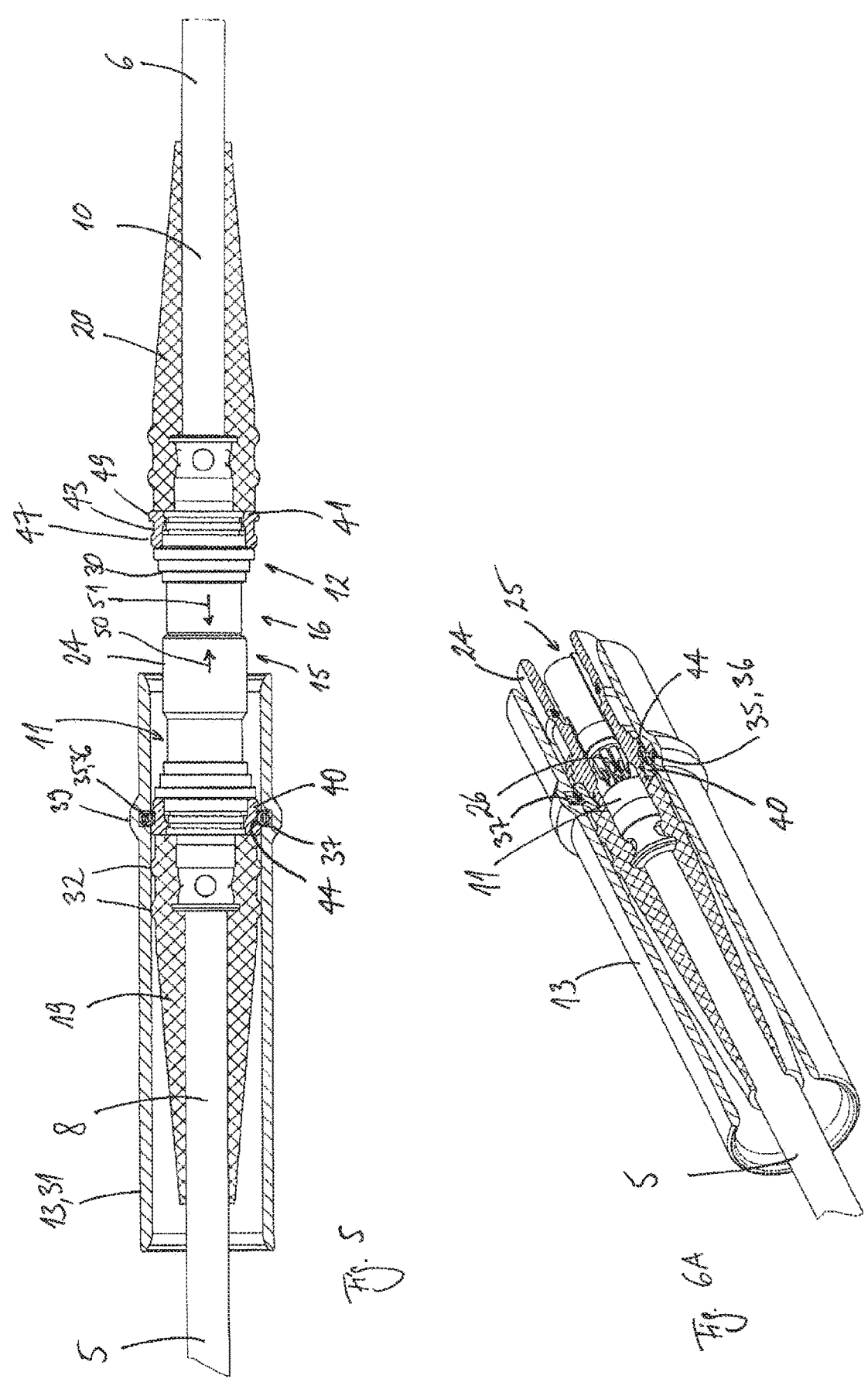

FIGS. 2A through 6B show the system 1 or individual components of the system 1 from FIGS. 1A through 1C according to example 1. FIGS. 4A and 4B show the system 1 according to example 1 in a configuration in which the connectors 11, 12 are connected and the securing sleeve 13 is in the securing position. FIG. 5 shows the system 1 according to example 1 in a configuration in which the connectors 11, 12 are connected and the securing sleeve 13 is in the holding position. FIGS. 6A through 6C show the connector 11 of the system 1, that is the system 1 according to example 1, in a configuration in which the connectors 11, 12 are separated and the securing sleeve 13 is in the holding position.

In the example 1 of the system 1 shown in FIGS. 2A through 6B, the first connector 11 and the second connector 11 each comprises a housing 17, 18 that is formed of a metal material such as, for example, titanium or stainless steel. Both connectors also have sleeve-shaped anti-kink protection 19, 20, through which the respective second end 7, 9 of the first or second element 5, 6 runs, to prevent, to the maximum possible extent, kinking. The anti-kink protection 19, 20 is solidly connected with the housing 17, 18 of the respective connector 11, 12 at the back end 21, 22 of the respective connector 11, 12.

The first connector 11 is configured in the form of a socket and the second connector 12 is configured in the form of a plug. The second connector 12 configured in the form of a plug has, at its front end 16, a coupling element 23 that is configured in the form of a sleeve. The first connector 11 that is configured in the form of a socket has, at its front end 15, a receiving part 24 for the coupling element 23 of the plug, this receiving part 24 also being sleeve-shaped. If the connectors 11, 12 are connected with one another, as is shown in FIG. 4A, the coupling element 23 is received in a holding area 25 defined by the receiving part 24.

The connectors 11, 12 have corresponding contact elements 26 that are configured to transfer electrical and/or optical signals and are arranged on the surfaces of the coupling element 23 or the receiving part 24 so that they are in contact with one another when the two connectors 11, 12 are connected with one another. Each of the contact elements 26 is connected with one of the conductors (not shown) of the respective cable.

The detachable connection between the two connectors 11, 12 can be made and released again practically as often as desired. The two connectors 11, 12 are equipped with a self-locking push-pull mechanism. For instance, in the example shown, the second connector 12 has, at its front end 16, on coupling element 23, multiple metal locking elements 27, which have latch elements 28 that point radially outward. The first connector 11 has multiple counter locking elements (not shown) that correspond with the locking elements 27 and that are configured, for example, in the form of recessed receiving areas on an inside surface of the metal receiving part 24. The locking elements 27 are movably connected with the housing 18 of the second connector 12 through articulations 28, which are formed by flexible elastic areas of the housing 18. The locking elements 27 are movable between a predefined locking position and a predefined unlocking position. The connection between the two connectors 11, 12 is only detachable if the locking elements are in the unlocking position, or can move into it.

The second connector 12 has a movable control element 30 that is connected with the locking elements 27. Manual manipulation (for example, axially pulling the control element 30 toward the back end 22 of the second connector 12) can move the locking element 27 from the locking position into the unlocking position. If the control element is not manipulated, the locking elements 27 are in the locking position (due to the elastic articulations 29) or move into it by themselves. That is, if the front ends 15 and 16 of connectors 11, 12 are pushed into one another (plug in socket) in the axial direction (with the contact elements 26 having the correct rotational orientation according to the markings 50, 51 shown in FIG. 5), then the locking elements 27 engage into the respective receivers by themselves and the axially stable detachable connection between the two connectors 11, 12 is created and automatically locked.

Figure 3A:
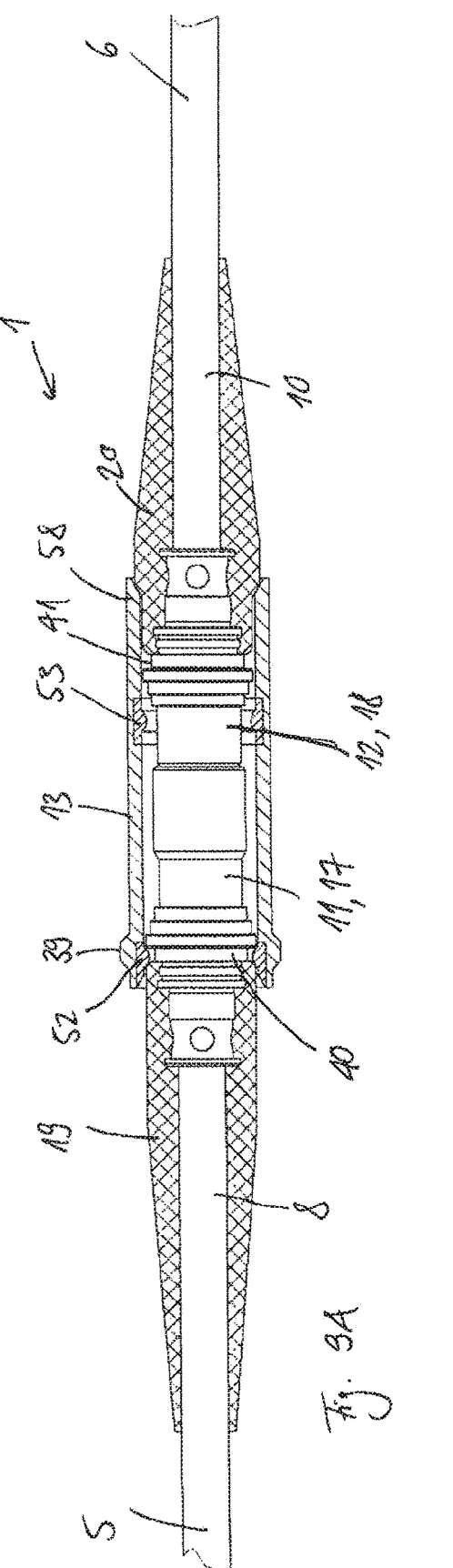
FIGS. 3A and 3B: a perspective illustration and a sectional view, respectively, of the securing sleeve of the system
Figure 3C:
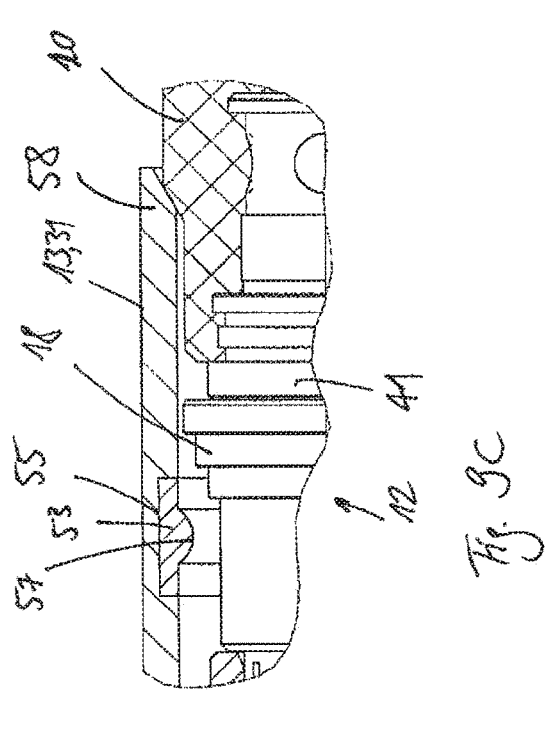
Figure 3B:
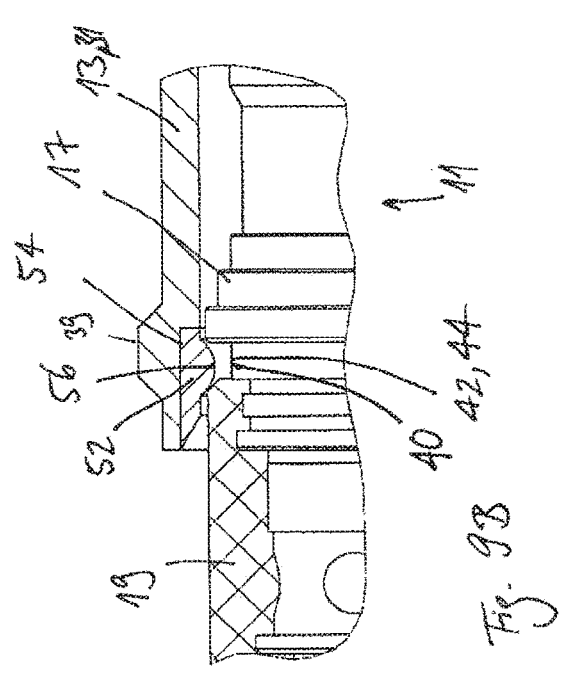

The securing sleeve 13 shown in FIGS. 3A and 3B has a sleeve-shaped main body 31, which forms the above-described hollow space 14 that is intended, in the securing position, to receive and cover the two front ends 15, 16 of the connectors 11, 12, including the locking elements 27, counter locking elements, and the control element 30. The fact that the control element 30 is inaccessible, and thus also cannot (unintentionally) be manually manipulated, as long as the securing sleeve 13 is in the securing position, protects the connection between the connectors from an (unwanted) unlocking and release. The fact that the sleeve 13 has engaged in the securing position prevents unwanted movement of the sleeve out of the securing position and unwanted unlocking of the connection of the connectors, which is, in principle, made possible as a result, or at least makes this more difficult.

The connectors 11, 12 and the securing sleeve 13 of the following examples 2 through 5 correspond to the connectors 11, 12 shown in FIGS. 2A, 2B and to the securing sleeve 13 of example 1 shown in FIGS. 2A, 2B and to the securing sleeve 13 of example 1 shown in FIGS. 3A and 3B, at least in the above-described features. Differences between the examples 1 through 5 result from different embodiments of the latch device, the latch elements and counter latch elements, and possibly from other elements as described below.

In order to support and guide, in the radial direction, securing sleeve 13 of the example 1 shown in FIGS. 2A through 6B, the outside surfaces of the connectors 11, 12 have, for example, support surfaces 32, 33, which are configured, for example, in the form of ring-shaped ridges and/or preferably make contact (all around) like sealing surfaces with an inner surface 34 of the sleeve (see FIGS. 4A through 6B).

The latch device of the example 1 shown in FIGS. 2A through 6B comprises, as a latch element 35, a closed elastic ring element 36. In the first example shown, this is a coil spring that is wound in the shape of a ring. However, alternatively it could also be configured as an axial circlip or as an O-ring. As is shown in FIG. 3B, the inner surface 34 of the sleeve 13 has an annular groove 37, in which the ring element 36 is permanently fastened by residual stress. Corresponding to the annular groove 37, the sleeve 13 has, on its outer surface 39, a ring-shaped ridge as a structured handling surface 39 of the sleeve 13.

The latch device also comprises counter latch elements 40, 41, which are ring-shaped elements that form areas of an outer surface 42, 43 of the first or second connector 11, 12. The latch element 35 is configured to engage in an annular groove 44 in the outer surface 42 of the first connector 11 if the securing sleeve is in the holding position (see FIGS. 5 and 6A through 6C. The latch element 35, 36 is also configured to engage in an annular groove 45 on the outer surface 43 of the counter latch element 41 of the second connector 12, if the securing sleeve 13 is in the securing position (see FIGS. 4A and 4B. A reverse configuration would also be possible (counter latch elements 40, 41 connected with sleeve 13, latch element 35 solidly connected with the first or second connector 11, 12).

The latch element 35 and the counter latch elements 40 and 41 are configured so that the securing sleeve 13 is movable out of the securing position and out of the holding position by manual axial displacement, if an axial displacement force acting on the securing sleeve 13 exceeds a predefined threshold. In particular, the counter latch elements form ascending surfaces 46, 47, which facilitate sliding of the latch element 35 into the respective annular groove 44 or 45, and each of them forms a (terminal) stop 48, 49, which prevents an unwanted axial displacement of the sleeve 13 beyond the securing position or holding position, so that the sleeve 13 can only be moved between the securing position and the holding position if the connectors 11, 12 are connected with one another.

As is shown in FIG. 5, each of the front ends 15, 16 of the first and second connector 11, 12 has an (arrow-shaped) marking 50, 51 arranged on it, with which it is possible to check a correct rotational orientation of the connectors to one another. The markings 50, 51 are advantageously easily visible for the user, if the sleeve 13, is in the holding position, as is shown in FIG. 5A.

FIGS. 7A through 10 show the system 1 from FIGS. 1A through 1C or individual components of it according to example 2. FIGS. 9A through 9D show the system 1 according to example 2 in a configuration in which the connectors 11, 12 are connected and the securing sleeve 13 is in the securing position. FIG. 10 shows the system 1 according to example 1 in a configuration in which the connectors 11, 12 are connected and the securing sleeve 13 is in the holding position.

In contrast to example 1, the latch device of example 2 has multiple latch elements, namely a first latch element 52 and a second latch element 53. These are configured in the shape of a ring, and are made of an elastic first plastic. In the first variant of the sleeve 13 shown in FIG. 8B and in the second variant of the sleeve 13 shown in FIG. 8C, the sleeve 13 has a main body 31 that is made of a relatively rigid second plastic, the inner surface 34 of this main body 31 having a ring-shaped depression 54, 55 arranged on it, which partly receives the first latch element 52 and the second latch element 53, respectively. The latch elements 52, 53 have bulges 56, 57 that project radially inward. In the case of the first variant shown in FIG. 8B, each of the bulges 56, 57 is configured in the form of multiple little bumps that are spaced apart from one another in the azimuthal direction. In the case of the second variant shown in FIG. 8C, each of the bulges 56, 57 is configured in the form of a ring-shaped ridge. The sleeve 13 according to the first or second variant is, for example, a 2K injection-molded part, whose main body 31 and latch elements 52, 53 have been produced with the above-mentioned first and second plastic in a 2K injection-molding process.

Essentially the only difference between the connectors 11, 12 of example 2 and the connectors 11, 12 of example 1 is the counter latch element 40 corresponding to the latch elements 52, 53, the counter latch element 40 in example 2 being formed by an area on the surface 42 of the housing 17 of the first connector 11. In this area of the surface 42, the housing has an annular groove 44, into which the first latch element 52 with the bulges 56 in the form of little bumps (variant 1) or the ring-shaped bulge 56 (variant 2) engages when the sleeve 13 is in the securing position (see FIGS. 9A through 9C), and into which the second latch element 52 with the bulges 56 in the form of little bumps (variant 1) or the ring-shaped bulge 56 (variant 2) engages when the sleeve 13 is in the holding position (see FIG. 10).

As can clearly be seen in FIGS. 9A and 9C, the outside diameter of the anti-kink protection 20 of the second connector 12 is dimensioned so that when the securing sleeve 13 is in the securing position, a front end 58 of the sleeve touches the anti-kink protection 20 from the outside and in this way is radially supported and stabilized by the anti-kink protection 20. As can clearly be seen in FIGS. 9A and 9C, the outside diameter of the anti-kink protection 19 of the first connector 11 is only slightly smaller than an inside diameter of the inner surface 34 of the sleeve 13, so that when the securing sleeve 13 is in the holding position it is radially supported and stabilized by the anti-kink protection 19.

Figure 17:
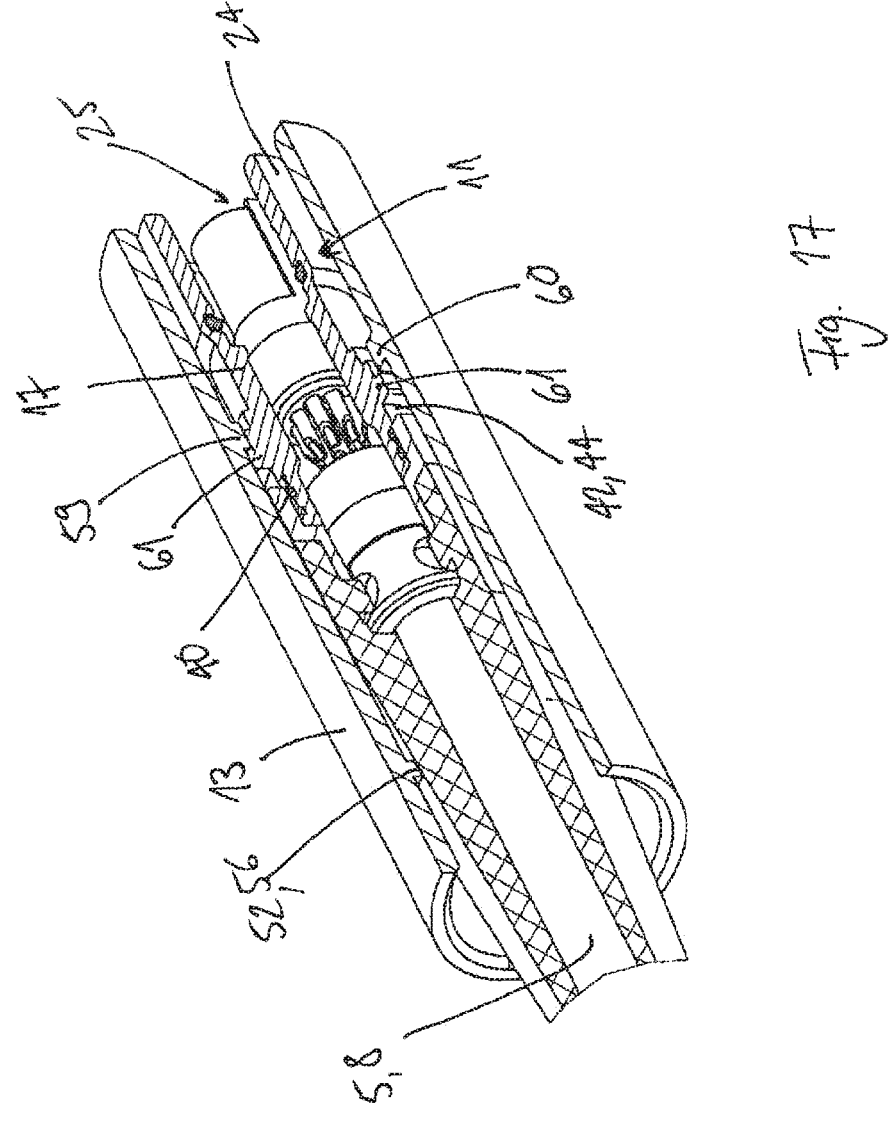
FIG. 17 a perspective sectional view of the first connector and the securing sleeve according to example 3 in a separated configuration, in which the securing sleeve is in a holding position and in the untensioned initial state.

FIGS. 11A through 17 show the system 1 from FIGS. 1A through 1C or individual components of it according to example 3. FIGS. 14A and 14B show the system 1 in a configuration in which the connectors 11, 12 are connected and the securing sleeve 13 is in the securing position. FIG. 15 shows the system 1 in a configuration in which the connectors 11, 12 are connected and the securing sleeve 13 is between the securing position and the holding position. FIGS. 16A through 17 show system 1 in a configuration in which the connectors 11, 12 are separated and the securing sleeve 13 is in the holding position.

The latch device in example 3 comprises, similarly to that in example 2, latch elements in the form of bulges 56 which project radially inward from an inner surface 34 of the sleeve 13. The bulges 56 are configured in the form of ridges. See FIGS. 11A and 11B.

FIG. 12B shows the securing sleeve 13 in an untensioned initial state that it assumes when no external force, in particular no radial compressive force, acts on it. When the securing sleeve 13 is in the initial state, the two bulges 56 assume a first distance D1 from one another. The first radial distance D1 is defined in a first radial direction and is dimensioned so that the two bulges 56 in the surface 42 of the first connector 12, which in this example is formed by a counter latch element 40 provided with an annular groove 44, engage or are engaged if the securing sleeve 13 is in the initial state and is in the securing position relative to the first connector 11 and the second connector 12 connected with the first connector 11. As is shown in FIGS. 14A and 14B, the two bulges 56 then enter into this annular groove 44.

As is shown in FIG. 12A, the securing sleeve 13 is deformable into a tensioned intermediate state by a radial compressive force F that acts on the securing sleeve 13 in a second radial direction that is different from the first radial direction. This compressive force can be produced by manual compression. When the securing sleeve 13 is in the intermediate state, the two bulges 56 assume a second distance D2 from one another defined in the first radial direction. The second distance D2 is greater than the first distance and is dimensioned so that the two bulges are not (any longer) engaged in the surface 40 of the first connector 11 (that is, they then do not enter into the annular groove 44) when the securing sleeve 13 is in its intermediate state and simultaneously in the securing position. To accomplish this, D2 is (at least slightly) larger than a largest outside diameter of the housing 17 of the first connector 11. Therefore, when the sleeve 13 is in this intermediate state it can be moved, by axial displacement relative to the first and second connector 11, 12, into the securing position or back out of it, as is shown in FIG. 15. The mentioned deformation of the sleeve 13 is elastic, so that the securing sleeve 13 deforms by itself back into the initial state shown in FIG. 12B as soon as the radial compressive force F is no longer acting on it.

The sleeve 13 also has, on its inside surface 34, first bulges 59 and second bulges 60, which interact with a stop 61 that is arranged on the first connector 11 to allow the sleeve 13 to be pushed from the securing position as far as the holding position defined by this stop 61, as is shown in FIGS. 16A and 16B, but no farther, and to allow this irrespective of whether the sleeve is in the initial state or in the intermediate state. To accomplish this, the first bulges 59 are, for example, arranged and dimensioned in such a way that their distance in the first direction is less than the outside diameter of the stop 61 in the first direction, if the securing sleeve 13 is in the initial state, as is shown in FIG. 13A. Moreover, the second bulges 60 are arranged and dimensioned in such a way that their distance in the second direction is less than the outside diameter of the stop 61 in the second direction, if the securing sleeve 13 is in the intermediate state, as is shown in FIG. 13B. As is shown in FIGS. 12B and 13B, the cross section of the main body of the sleeve 13 is oval-shaped in the initial state and circular in the intermediate state, as is shown in FIGS. 12A and 13B. The stop 61 has, for example, a circular outer contour with an outside diameter that approximately corresponds to, or is slightly smaller than D2.

FIGS. 18A through 21B show the system 1 from FIGS. 1A through 1C or individual components of it according to example 4. FIGS. 19A and 19B show the system 1 according to example 4 in a configuration in which the connectors 11,

12 are connected and the securing sleeve 13 is in the securing position. FIGS. 20A and 20B show system 1 in a configuration in which the connectors 11, 12 are connected and the securing sleeve 13 is in the holding position. FIGS. 21A and 21B show system 1 in a configuration in which the connectors 11, 12 are separated and the securing sleeve 13 is in the holding position.

Example 4 differs from examples 1 through 3 in that the securing sleeve 13 of system 1 has, at its front end 58, multiple latch arms 61 extending in the axial direction, each of which has a latch element 52 of the latch device in the form of a latch tooth 63 that projects radially inward. Each of the latch arms 61 also has another latch element 53 in the form of a bulge 60 that points radially inward.

An area of the surface 42 of the second connector 12 is formed by a ring-shaped handling part 64 that is made from a plastic, for example, and that also forms a counter latch element 41 for the latching teeth 63.

The counter latch element 41 has a step 65. If the sleeve 13 is in the securing position, as shown in FIGS. 19A and 19B, the latch teeth 63 of the latch arms 62 reach behind the step 65. As can be seen in FIG. 21B, the counter latch element 41 has unlocking ascending surfaces 66, which border the back of the step 65. When the sleeve 13 is in the securing position, (azimuthal) rotation of it causes the latch arms 62 to slide over the unlocking ascending surfaces 66, spreading them apart in the radial direction, the latching teeth 63 of the latch arms 62 making contact with the unlocking ascending surfaces 66.

As can be seen in FIG. 19B, the latch arms 62 have, on the front surface of the respective latch tooth 63, an ascending surface 67 and, on the back surface of the respective latch tooth 63, a support surface 68.

While the support surfaces 68 are oriented essentially perpendicular to the longitudinal axis of the sleeve 13, the ascending surfaces 67 are bent at an angle to it so that the securing sleeve 13 can be pushed into the securing position by axial displacement of the securing sleeve 13. However, the sleeve 13 can only be moved back out of the securing position after the above-described rotation and sliding motion over the unlocking ascending surfaces.

The other latch elements 53 also have, on the front or back surfaces of the respective bulges 60, ascending surfaces 67 and support surfaces 68, all of which are bent at an angle so that the securing sleeve 13 can be moved into the holding position and back out of it by axial displacement, if a defined displacement force is applied. In the holding position, the latch elements 53 interlock with a corresponding counter latch element 40 of the first connector 11. The counter latch element 40 forms an area of the surface 42 of the first connector 11 and has an annular groove 44 which receives the bulges 60 if the sleeve 13 is pushed in the holding position.

Figures 23A, 23B:
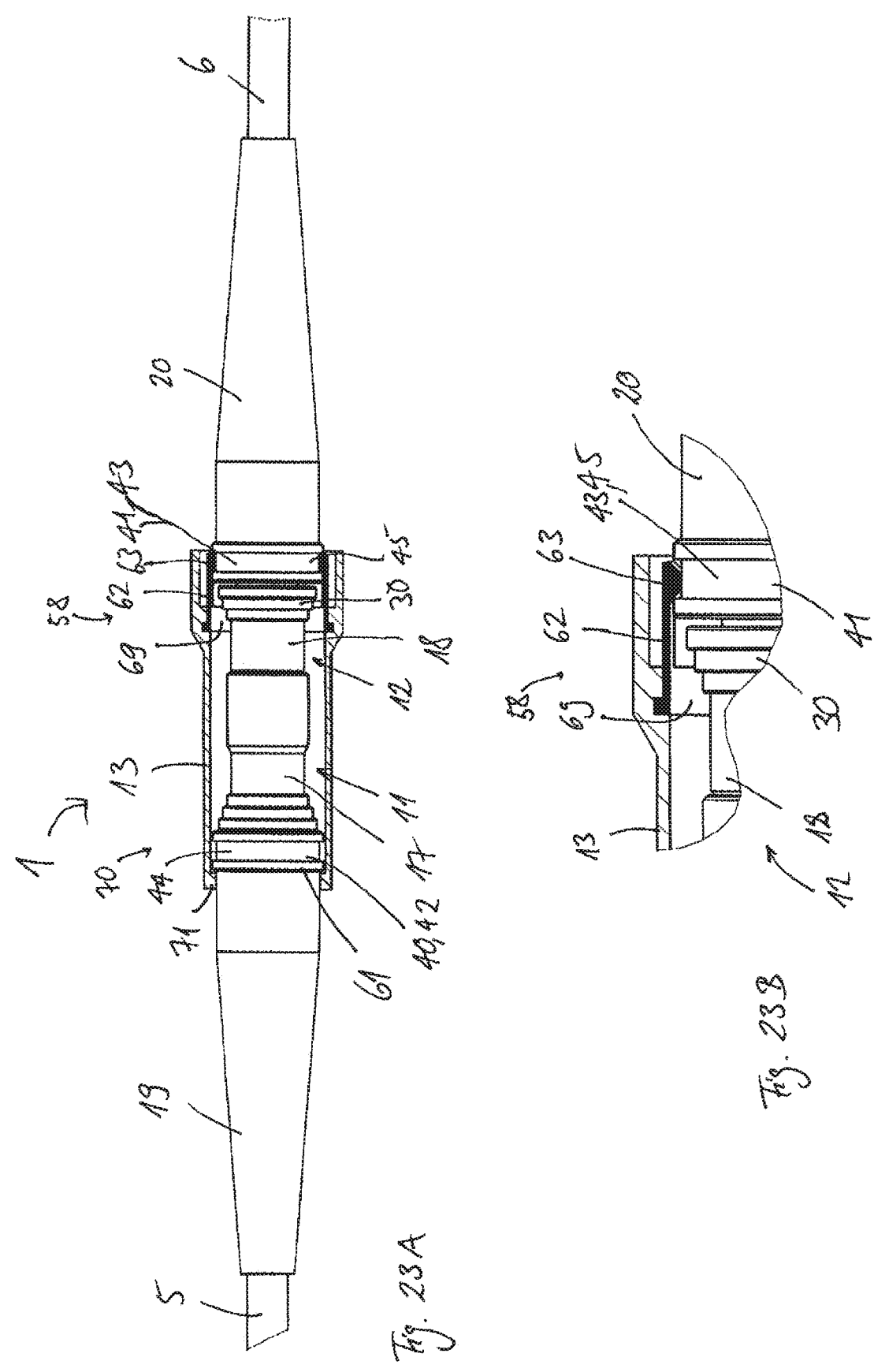
Figures 24A, 24B:
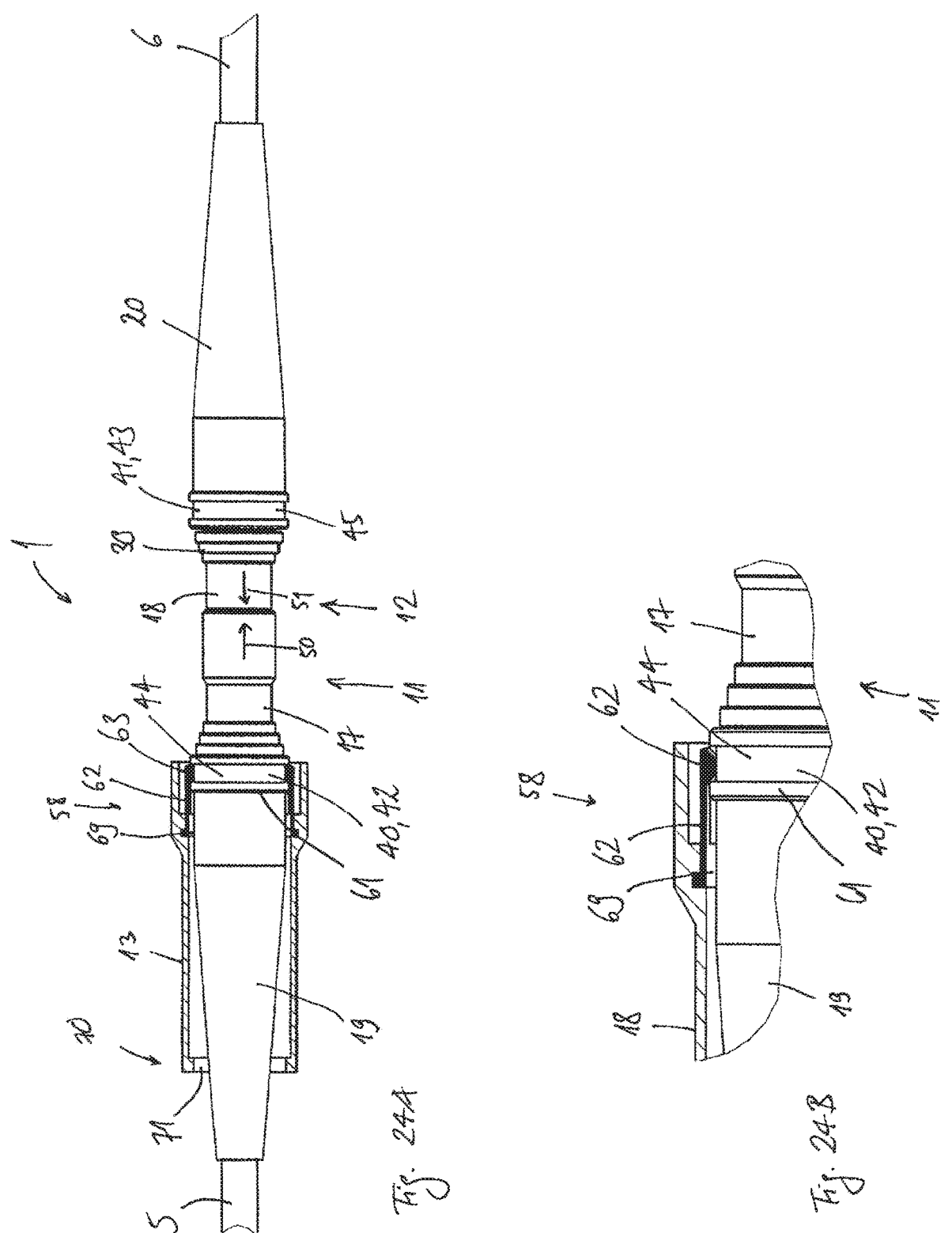

FIGS. 22A through 24A show the system 1 from FIGS. 1A through 1C or individual components of it according to example 5. FIGS. 23A and 23B show the system 1 in a configuration in which the connectors 11, 12 are connected and the securing sleeve 13 is in the securing position. FIGS. 24A and 24B show system 1 in a configuration in which the connectors 11, 12 are connected and the securing sleeve 13 is in the holding position.

As in example 4, in example 5 the securing sleeve 13 also has, at its front end 58, multiple latch arms 62 extending in the axial direction, each of which has a latch element of the latch device in the form of a latch tooth 63 that projects radially inward. While the latch arms 62 in example 4 are configured as axial extensions of the essentially cylindrical main body 31 of the sleeve 13, the latch device in example 5 has a sleeve-shaped support 69, made of a metal material, for example (see FIG. 22B), starting from which the latch arms 62 extend in the axial direction. The support 69 is solidly connected with the main body 31 of the sleeve 13, for example by cementing or form-fit joining or pressing. The support is arranged in the hollow space 14 defined by the main body 31 of the sleeve 13, just as the latch arms 62 are.

The second connector 12 of example 5 differs from the second connector 12 of example 4 in that the counter latch element 41 in example 5 does not have any unlocking ascending surfaces 66 on the back surface of the step 65. To allow unlocking without rotation of the sleeve in example 5, instead of this the back (planar) support surfaces 68 of the latch teeth 63 are bent at an angle with respect to a reference plane that is oriented perpendicular to the longitudinal axis of the securing sleeve 13. Preferably the angle that is respectively included between the support surface 68 and the reference plane lies between 30° and 60°, in this case, for example about 45°. This defines the force that is required to push the sleeve 13 out of the securing position in the axial direction. As is shown in FIG. 23B, the support surface of the annular groove 45 can be oriented, for example, at an angle of 90° to the longitudinal axis of the second connector 12. However, alternatively it is also possible to make the annular groove 45 of the surface 43 of the latch element 41 bent at an angle. The same also goes for the support surface of the annular groove 44 of the surface 42 of the latch element 40.

As is shown in FIG. 24A, the sleeve 13 can be pushed, by axial displacement, into the holding position, in which the latch teeth 63 engage in the annular groove 44 on the surface 42 of the first connector 11, this annular groove 44 being formed by the counter latch element 40. When the support surfaces 68 engage in the holding position, they can now act as ascending surfaces, due to their angled orientation. In comparison with example 4, this makes it possible to do without the additional latch elements 53 on the latch arms 62 for the engagement of the sleeve 13 in the holding position.

Figures 22A, 22B:
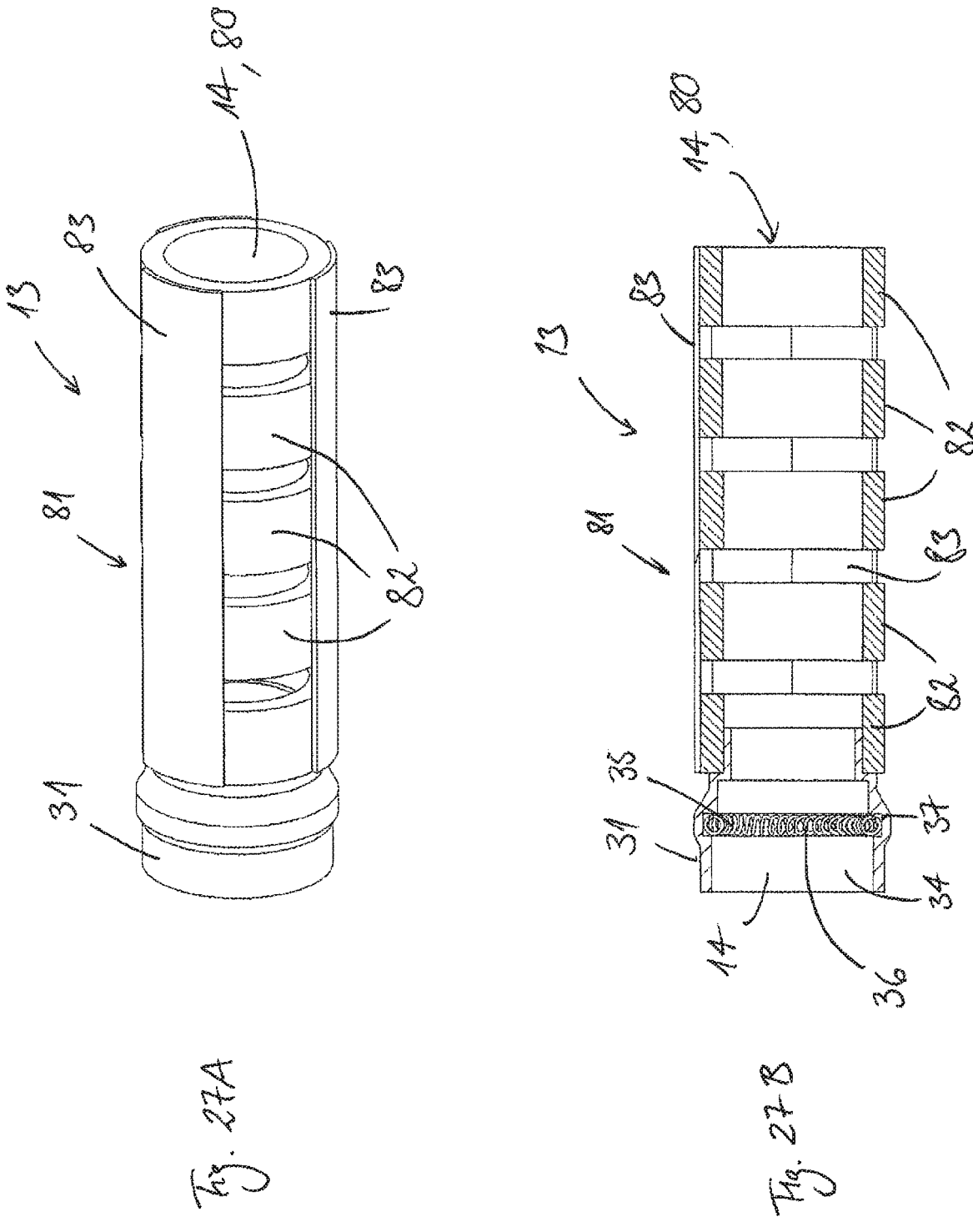
FIG. 22A a perspective sectional view of the securing sleeve of the system shown in FIG. 1, according to a fifth sample embodiment (example 5)
FIG. 22B a support integrated into the securing sleeve according to example 5.

As can be seen in FIG. 22A, for example, the sleeve 13 has, on the inner surface 34 of its back end 70, a ridge-shaped bulge 71 that is directed radially inward and that interacts with a stop 61 on the first connector 11 to prevent the sleeve 13 from completely slipping off the first connector 13, and thus loss of the sleeve 13.

Figures 25A, 25B, 25C:
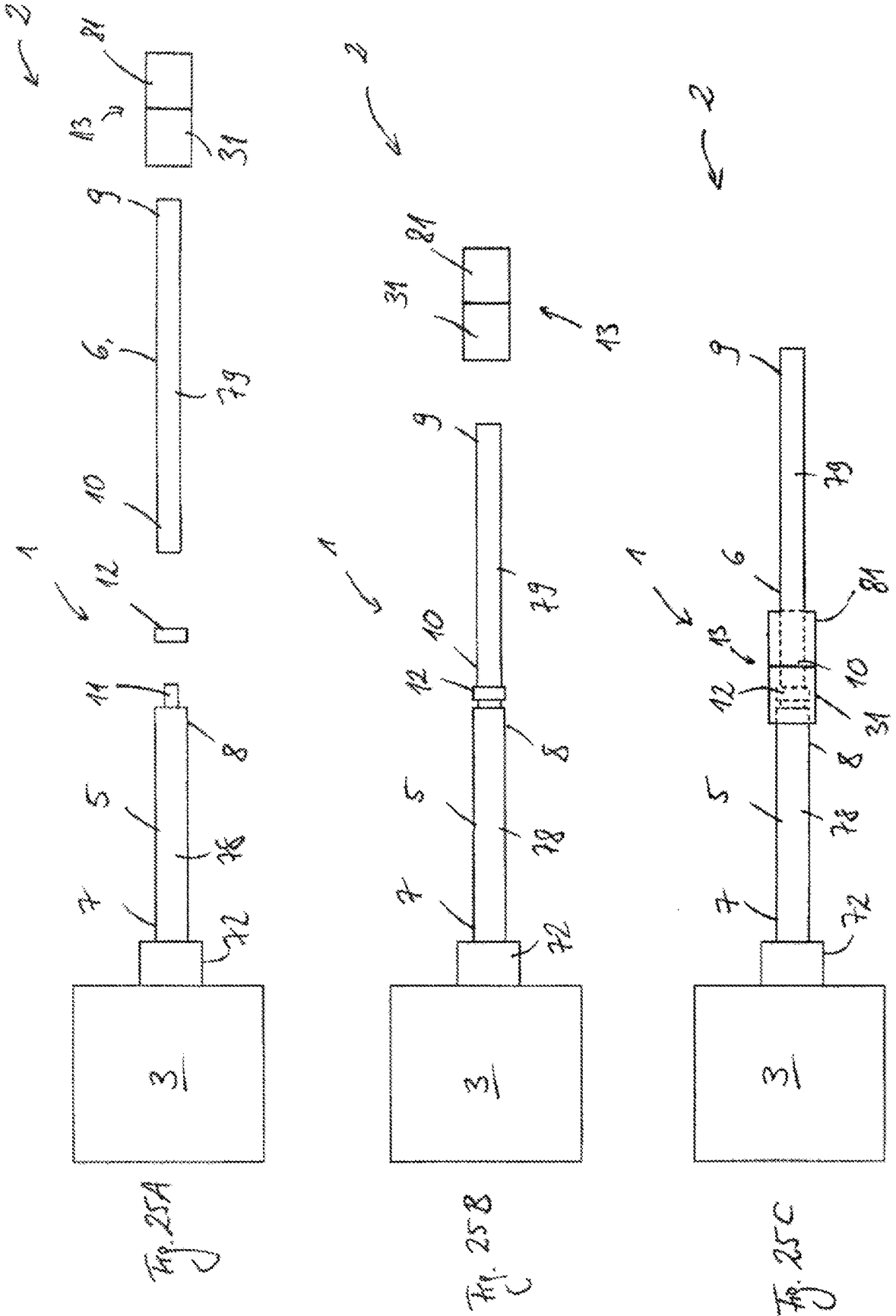
FIG. 25A a schematic illustration of a system of the type suggested here as a component of a blood pump system of the type suggested here in a separated configuration.
FIG. 25B the system and blood pump system shown in FIG. 25A in a connected and released configuration.
FIG. 25C the system and blood pump system shown in FIGS. 25A and 25B in a connected and secured configuration.

Each of FIGS. 25A through 25C shows a schematic representation of another (second) system 1 of the type suggested here for securing a releasable connection between two elements 5, 6 configured as hollow bodies 78, 79. This system 1 is, for example, a component of another blood pump system 2 of the type suggested here. In principle, the blood pump system 2 shown in FIGS. 1A through 1C and 25A through 25C can be one and the same blood pump system 2. That is, in this case, the blood pump system 2 comprises two systems 2 of the type suggested here, the first system 1 as described above securing the detachable connection between two elements 5, 6 configured as cables, and the second system 2, as described below, securing the detachable connection between the two elements 5, 6 of the blood pump system 2 configured as hollow bodies 78, 79. However, the blood pump system 2 can also comprise only the first or only the second of these two systems 2.

The blood pump system 2 shown in FIGS. 25A through 25C comprises an implantable blood pump 3. The first element 5 is a pump-side hollow body 78 which has a first end 7 that is connectable in a fluid-tight manner or is connected in a fluid-tight manner with a pump outlet 72 of the blood pump 3, and which also has a second end 8. The second element 6 in the form of the other hollow body 79 has a first end 9 that is connectable, for example, with a blood vessel or heart of a patient, and also has a second end 10. Thus, each of the two elements 5, 6 forms a flow channel 74 or 75 to carry blood. See, for example, FIG. 29B.

The hollow body 78 of the first element 5 is, for example, a tube or a pipe. The hollow body 78 is, for example, made of silicone or another biocompatible material. However, the first element 5 could also be a part of the blood pump 3 or a part of the pump outlet 72, for example an outlet nozzle of the blood pump 3.

The hollow body 79 of the second element 6 is, for example, an implantable cannula, for example a vascular prosthesis made of a graft material, that is, a graft. For example, the hollow body 79 has a tubular textile support structure. Before its use, this can be sealed with a sealing material, such as, for instance, bovine gelatin, or also be sealed only once it is soaked with blood (so-called glotting).

The system 1 is set up to connect the two elements 5 and 6, that is hollow bodies 78, 79, with one another in a detachable and fluid-tight manner, so that the two flow channels 74, 75 form a continuous flow channel. See, for example, FIGS. 26A, 26B. To accomplish this, the system 1 comprises a first connector 11 and a second connector 12.

In FIGS. 25B and 25C, the two connectors 11, 12 and the two elements 5, 6 are connected with one another. In FIG. 25A the two connectors 11, 12 and the two elements 5, 6 are separated from one another.

Figures 26A, 26B:
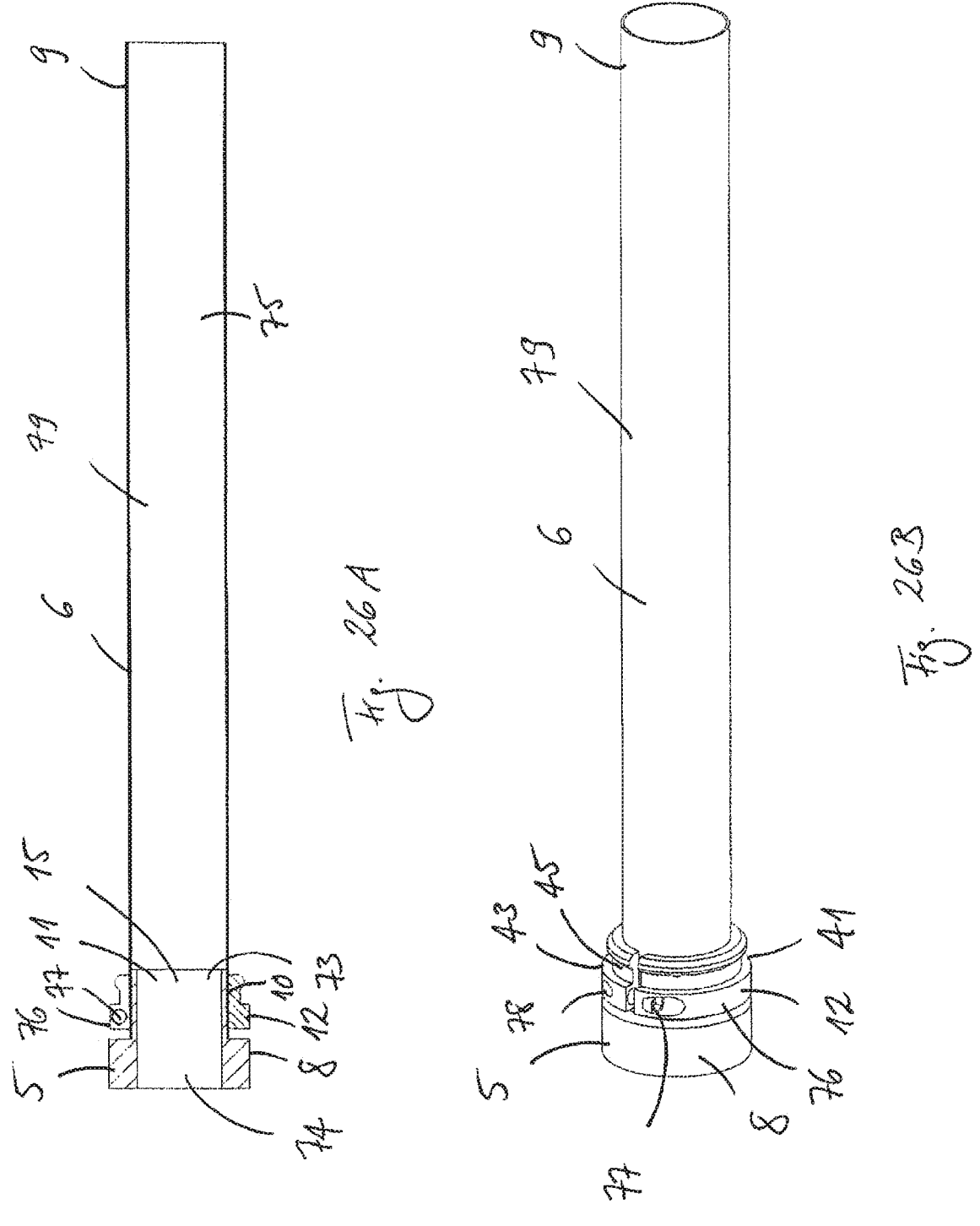
FIGS. 26A and 26B: a longitudinal section and a perspective illustration, respectively, of examples of elements and connectors of the system and blood pump system shown in FIGS. 25A through 25C, each in a connected and non-secured state.

As is shown in FIG. 26A, the first connector 11 can be configured as a tubular element 73 that is arranged at the second end 8 of the first element 5. (The first element 5 is only partly shown in FIGS. 26A through 29B.) In the example shown, the first connector 11 or the tubular element 73 is solidly connected with the first element 5 and is, for example, made as a single piece with the first element 5. In principle, the first connector 11 or the tubular element 73 can be formed by an axial end section of the first element 5 at its second end 8, at which the first element 5 can have, for example, a reduced outside diameter, as is shown in FIG. 26A.

As is also shown in FIG. 26A, the outside diameter of the first connector 11 and the inside diameter of the second element 6 are matched with one another so that the front end 15 of the first connector 11 can be pushed in the axial direction into the flow channel 75 of the second element 6.

As is shown in FIGS. 26A and 26B, the second connector 12 can be configured, for example, as a clamping element 26, for example, in the form of a hose clamp 76 or in the form of a split sleeve. The second connector 12 is typically configured so that it can surround the second end 10 of the second element 6 and, inserted into it, the front end 15 of the first connector 15, to exert a clamping force onto these parts. In this case, the second connector 12 or the clamping element (hose clamp) 76 can be put into a tensioned state, to exert, onto the second element 6, a clamping force that acts radially inward, and thus a fluid-tight clamping connection, between the second element 6 and the first connector 11. For example, to make and/or to stabilize the tensioned state, the second connector 12 (clamping element, hose clamp 76) has a screw-type connection with a tightening screw 77 and a corresponding threaded part. Alternatively, the second connector 12 or the tensioning element (hose clamp) 76 could also comprise a latch-type connection with corresponding latch elements or an elastic spring element. For example, the second connector 12 or the clamping element (hose clamp) 76 is made of a metal and/or a polymer.

The system 1 also comprises a securing sleeve or sleeve 13. The sleeve 13 comprises a sleeve-shaped main body 31 and a protective element 81. The protective element 81 forms anti-kink protection and cutting protection for the second element 6 or the second hollow body (graft) 79.

In this example, the securing sleeve 13 can be pushed over the first end 9 of the second element 6 and onto the second element 6, and then be axially displaced as far as the second end 10 of the second element 6. See, for example, FIG. 28. In principle, axial displacement in the opposite direction can also push the securing sleeve 13 back down off the second element 6, and separate it.

Figures 28, 29A, 29B:
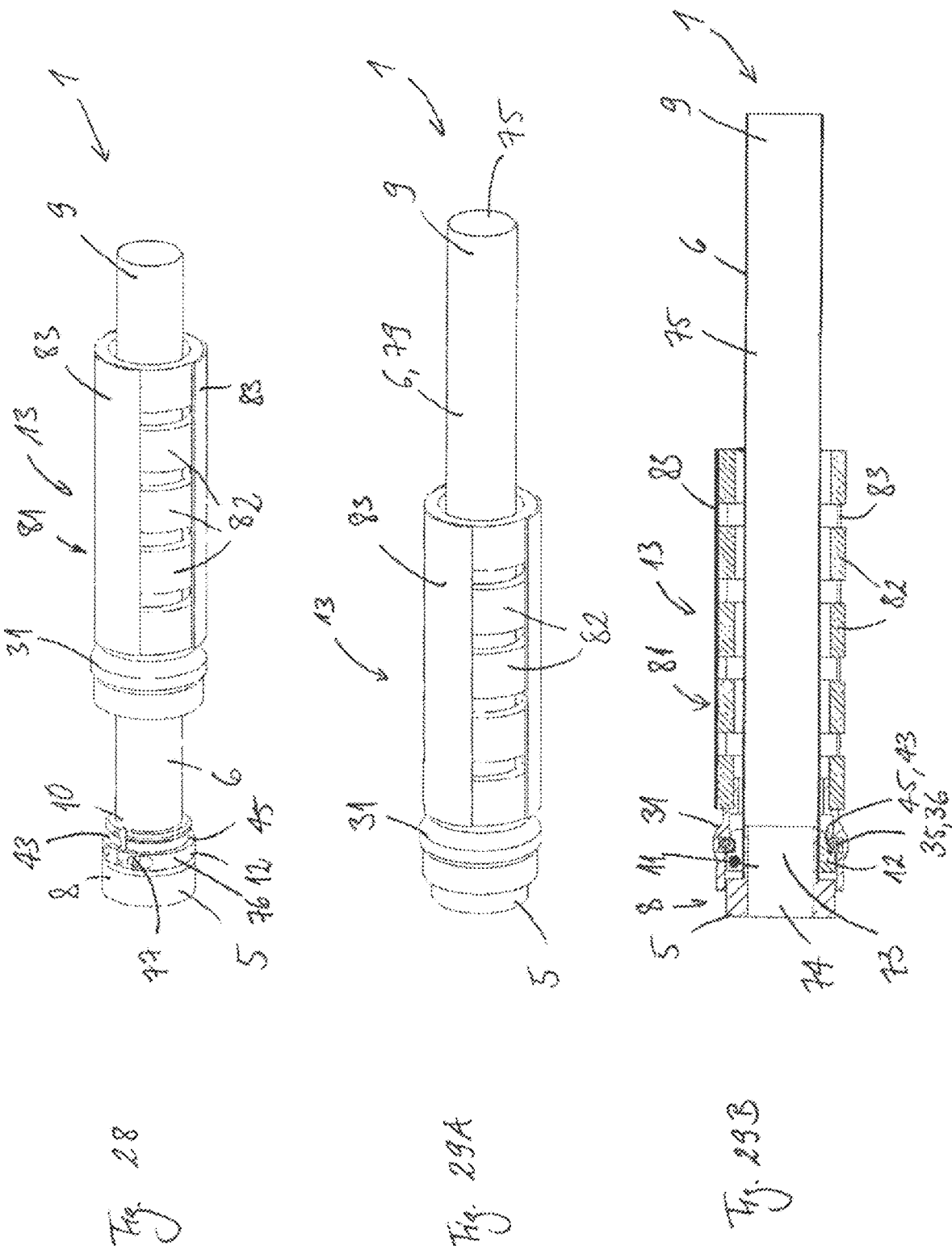
FIG. 28 a perspective illustration of the components shown in FIGS. 26A through 27B, wherein the securing sleeve is axially displaced along the second element.
FIGS. 29A and 29B: a perspective illustration and a longitudinal section of the components shown in FIGS. 26A through 28, wherein the securing sleeve is in the securing position.

If the first connector 11 is connected with the second connector 12, as is shown in FIGS. 25B and 25C and in FIGS. 28, 29A, and 29B, the sleeve 13 is movable into a securing position by manual axial displacement of the securing sleeve 13 relative to the first connector 11 and the second connector 12. This configuration is shown in FIG. 25C and in FIGS. 29A and 29B.

As is shown in FIG. 25C and in FIGS. 29A and 29B, when the securing sleeve 13 is in the securing position, it receives each of the first connector 11 and the second connector 12, and in the example shown it even does so completely, and thus covers the first and second connectors 11, 12. For this purpose, the securing sleeve 13 defines a hollow space 14, which completely and continuously passes through the securing sleeve 14 in the axial direction. The hollow space 14 runs through the sleeve-shaped main body 31, and is continued in the protective element as channel 80.

The protective element 81 can be configured, for example, as one of the protective elements suggested in European patent application EP 16 16 4527.0. For example, the protective element 31 comprises multiple segments 82, which are arranged next to one another in a sequence. Each of the segments 82 defines a partial section of the channel 80 of the protective element 81. The segments 82 are made of a relatively soft silicone (for example Shore A 30-90). The segments 82 can be injection-molded parts, for example. By contrast, the main body 31 of the securing sleeve 13 is made, for example, of a relatively hard silicone (preferably Shore B-C).

The protective element 81 has multiple (for example, three) connection elements 83 also made of silicone, which connect the segments 82 with one another. To accomplish this, the connection elements 83 are cemented with the segments 82. The connection elements are configured in the form of bands, that is, they form flat, cable-shaped elements. The connection elements 83 are arranged spaced apart from one another in a peripheral direction around the protective element 81. The main body 31 of the securing sleeve 13 is cemented with the frontmost segment 82, and thus is connected as a whole by material bonding with the securing element 31.

The system 1 also comprises a latch device with a latch element 35 and a counter latch element 41. See, for example, FIGS. 27B and 29B. The latch device or the latch element 35 and the counter latch element 41 are configured to create a latch connection between the securing sleeve 13 and the second connector 12, if the securing sleeve is in a securing position relative to the first connector 11 and relative to the second connector 12. This configuration is shown in FIG. 25C and in FIGS. 29A and 29B.

The securing sleeve 13 has, on an inner surface 34 of the main body 31, an annular groove 37, in which the mentioned latch element 35 of the latch device is arranged. See FIGS. 27B and 29B. The latch element 35 is configured, for example, in the form of an elastic ring element 36, for example in the form of a coil spring that is wound in the shape of a ring and that has, in an initial shape (with no force applied to it) an elliptical cross section, for example.

As the counter latch element 41 for the elastic ring element 36, the second connector 12 configured in the form of a hose clamp 76 has, on its outer surface 43, a corresponding annular groove 45. See FIGS. 26A and 26B and FIGS. 28 and 29B. The latch connection between the securing sleeve 13 and the second connector 12 is made by the latch element 35 entering into the counter latch element 41, if the securing sleeve 13 is in the securing position. See FIGS. 29A and 29B. This simultaneously also fixes the securing element 81 so that it receives a part of the second element in the channel 80 and thus protects it from damage (for example, due to unwanted cutting by a scalpel) and unwanted deformations (kinking, compression). This latch connection can be made or released again by a sufficiently large axial displacement force, without this requiring rotation.

LIST OF REFERENCE NUMBERS

1 System
2 Blood pump system
3 Blood pump
4 Control device
5 (First) element
6 (Second) element
7 First end
8 Second end
9 First end
10 Second end
11 First connector
12 Second connector
13 Securing sleeve (sleeve)
14 Hollow space
15 Front end
16 Front end
17 Housing
18 Housing
19 Anti-kink protection
20 Anti-kink protection
21 Back end
22 Back end
23 Coupling element
24 Receiving part
25 Receiving area
26 Contact elements
27 Locking element
28 Latch element
29 Joint
30 Control element
31 Main body
32 Support surface
33 Support surface
34 Surface
35 Latch element
36 Ring element
37 Annular groove
38 Surface
39 Handling surface
40 Counter latch element
41 Counter latch element
42 Surface
43 Surface
44 Annular groove
45 Annular groove
46 Ascending surface
47 Ascending surface
48 Stop
49 Stop
50 Marking
51 Marking
52 Latch element
53 Latch element
54 Depression
55 Depression
56 Bulge
57 Bulge
58 Front end
59 Bulge
60 Bulge
61 Stop
62 Latch arm
63 Latch tooth
64 Handling part
65 Step
66 Unlocking ascending surface
67 Ascending surface
68 Support surface
69 Support
70 Back end
71 Bulge
72 Pump outlet
73 Tubular element
74 Flow channel
75 Flow channel
76 Clamping element
77 Tightening screw
78 Hollow body
79 Hollow body
80 Channel
81 Protective element
82 Segment
83 Connection element To clarify the use of and to hereby provide notice to the public, the phrases "at least one of <A>, <B>, . . . and <N>" or "at least one of <A>, <B>, . . . <N>, or combinations thereof" or "<A>, <B>, . . . and/or <N>" are defined by the Applicant in the broadest sense, superseding any other implied definitions hereinbefore or hereinafter unless expressly asserted by the Applicant to the contrary, to mean one or more elements selected from the group comprising A, B, . . . and N. In other words, the phrases mean any combination of one or more of the elements A, B, . . . or N including any one element alone or the one element in combination with one or more of the other elements which can also include, in combination, additional elements not listed. Unless otherwise indicated or the context suggests otherwise, as used herein, "a" or "an" means "at least one" or "one or more."

The invention claimed is:

1. A blood pump system comprising:
a blood pump;
a first connector and a second connector, which is releasably connectable to the first connector;
a securing sleeve configured to be moveable, when the first connector is connected to the second connector, by displacement of the securing sleeve, relative to the first connector and relative to the second connector, to a securing position in which the securing sleeve completely or at least partially receives the first connector and the second connector;

a latching device with at least one latching element, wherein the latching device is configured to produce a latching connection between the securing sleeve in the securing position and the first connector and/or the second connector connected to the first connector;

a control device for the blood pump, a pump-side cable with a first end that is connectable with the blood pump, and with a second end; and a controller-side cable with a first end that is connectable with the control device, and with a second end, wherein the first connector is solidly connected with the second end of the pump-side cable and the second connector of the system is solidly connected with the second end of the controller-side cable;

wherein at least one of the at least one latching element of the latching device has a bulge, which projects radially inward starting from an inner surface of the securing sleeve, wherein the securing sleeve comprises a sleeve-shaped main body, and wherein the bulge is softer than the sleeve-shaped main body of the securing sleeve.

2. The system of claim 1, wherein at least one of the at least one latching element is configured:

to engage on a surface of the securing sleeve, when the securing sleeve is in the securing position.

3. The system of claim 1, wherein the at least one latching element comprises two latching elements each having a bulge that project radially inward from an inner surface of the securing sleeve, the two bulges assuming a first radial distance from one another when the securing sleeve is in an initial state, the first radial distance being defined in a first radial direction and being dimensioned so that the two bulges are engaged in a surface of the first connector or a surface of the second connector when the securing sleeve, in the initial state, is in the securing position relative to the first connector and to the second connector connected with the first connector, the securing sleeve being deformable into an intermediate state by a radial compressive force that acts on the securing sleeve in a second radial direction that is different from the first radial direction, the two bulges assuming a second distance from one another defined in the first radial direction when the securing sleeve is in the intermediate state, the second distance being greater than the first distance and being dimensioned such that the two bulges are not engaged in the surface of the first connector or the surface of the second connector when the securing sleeve is in the intermediate state relative to the first connector and to the second connector connected with the first connector, and is in the securing position.

4. The system of claim 1, wherein the latching device comprises at least one flexible latching arm.

5. The system of claim 1, wherein:

the first connector comprises a plug and the second connector comprises a coupling or socket, or wherein the first connector comprises a coupling or socket and the second connector comprises a plug.

6. The system of claim 5, wherein the plug and the socket are configured to be pushed into one another in an axial direction parallel to the aligned longitudinal axes of the first connector and of the second connector.

7. The system of claim 6, wherein the socket and the plug each comprises a sleeve, wherein the sleeve of the socket is configured to receive the sleeve of the plug when the plug and the socket are pushed axially into one another.

8. The system of claim 1, wherein the first connector and/or the second connector further comprises:

at least one locking element coupled with the releasable connection between the first connector and the second connector and configured to lock the releasable connection.

9. The system of claim 1, wherein the securing sleeve is movable relative to the first connector and/or relative to the second connector into a holding position that is different from the securing position by displacement of the securing sleeve relative to the first connector and/or relative to the second connector, further wherein the latching device is configured to make a second latching connection between the securing sleeve in the holding position and the first connector or the second connector, wherein the second latching connection between the securing sleeve in the holding position and the first connector or the second connector is different from the latching connection between the securing sleeve in the securing position and the first connector and/or the second connector.

10. The system of claim 9, wherein the bulge projecting radially inwardly from the inner surface of the securing sleeve is configured:

to engage on a surface of the first connector to establish the latching connection when the securing sleeve is in the securing position, and to engage on a surface of the second connector to establish the second latching connection when the securing sleeve is in the holding position.

11. The system of claim 10, wherein the securing sleeve is movable out of the securing position or the holding position by axial displacement of the securing sleeve, when an axial displacement force acting on the securing sleeve exceeds a predefined threshold.

12. The system of claim 9, wherein the bulge projecting radially inwardly from the inner surface of the securing sleeve is a component of the securing sleeve or solidly connected with the securing sleeve, so that the bulge is not released from the securing sleeve when the securing sleeve is moved out of the securing position or out of the holding position.

13. The system of claim 1, wherein at least one latching element of the at least one latching element of the latching device is configured as an elastic ring element that includes a coil spring that is wound in the shape of a ring.

14. The system of claim 1, wherein the bulge projecting radially inwardly from the inner surface of the securing sleeve is a component of the securing sleeve or is solidly connected with the securing sleeve, so that the bulge is not released from the securing sleeve when the securing sleeve is moved out of the securing position.

15. The system of claim 1, wherein at least one of the at least one latching element is configured:

to engage on a surface of the first connector.

16. The system of claim 1, wherein at least one of the at least one latching element is configured:

to engage on a surface of the second connector.

17. The system of claim 1, wherein:

the first connector comprises a tubular element and the second connector comprises a tensioning element or the second connector comprises a tubular element and the first connector comprises a tensioning element, wherein the tensioning element surrounds and exerts a clamping force on the tubular element.

18. The system of claim 1, wherein at least one latching element of the at least one latching element of the latching device is configured as an elastic ring element that includes a coil spring that is wound in the shape of an axial circlip.

19. The system of claim 1, wherein at least one latching element of the at least one latching element of the latching device is configured as an elastic ring element that includes a coil spring that is wound in the shape of an O-ring.

\* \* \* \* \*